US012599667B2

(12) United States Patent
Slichter

(10) Patent No.: US 12,599,667 B2
(45) Date of Patent: Apr. 14, 2026

(54) METHODS OF PREVENTING PLATELET ALLOIMMUNIZATION AND ALLOIMMUNE PLATELET REFRACTORINESS AND INDUCTION OF TOLERANCE IN TRANSFUSED RECIPIENTS

(71) Applicant: BLOODWORKS, Seattle, WA (US)

(72) Inventor: Sherrill J. Slichter, Vashon, WA (US)

(73) Assignee: BLOODWORKS, Seattle, WA (US)

( * ) Notice: Subject to any disclaimer, the term of this patent is extended or adjusted under 35 U.S.C. 154(b) by 590 days.

(21) Appl. No.: 17/955,515

(22) Filed: Sep. 28, 2022

(65) Prior Publication Data

US 2023/0097946 A1 Mar. 30, 2023

Related U.S. Application Data

(62) Division of application No. 16/303,578, filed as application No. PCT/US2017/035055 on May 30, 2017, now abandoned.

(60) Provisional application No. 62/342,831, filed on May 27, 2016.

(51) Int. Cl.

| | |
|---|---|
| ***A61K 41/17*** | (2020.01) |
| ***A01N 1/02*** | (2006.01) |
| ***A01N 1/124*** | (2025.01) |
| ***A01N 1/168*** | (2025.01) |
| ***A61K 35/14*** | (2015.01) |
| ***A61L 2/00*** | (2006.01) |
| ***A61M 1/02*** | (2006.01) |
| ***A61M 1/36*** | (2006.01) |

(52) U.S. Cl.

CPC .............. *A61K 41/17* (2020.01); *A01N 1/124* (2025.01); *A01N 1/168* (2025.01); *A61K 35/14* (2013.01); *A61L 2/0047* (2013.01); *A61L 2/0076* (2013.01); *A61M 1/0281* (2013.01); *A61M 1/3683* (2014.02); *A61L 2202/11* (2013.01); *A61L 2202/22* (2013.01); *A61M 2202/0427* (2013.01)

(58) Field of Classification Search

CPC ........ A01N 1/124; A01N 1/168; A61K 35/14; A61K 35/19; A61K 41/10; A61K 41/17; A61L 2/0047; A61L 2/0076; A61L 2202/11; A61L 2202/22; A61M 1/0281; A61M 1/3683; A61M 2202/0427

See application file for complete search history.

(56) References Cited

U.S. PATENT DOCUMENTS

| | | | |
|---|---|---|---|
| 6,258,577 | B1 | 7/2001 | Goodrich, Jr. et al. |
| 6,277,337 | B1 | 8/2001 | Goodrich, Jr. et al. |
| 7,648,699 | B2 | 1/2010 | Goodrich et al. |
| 7,901,673 | B2 | 3/2011 | Lockerbie et al. |
| 2001/0053547 | A1 | 12/2001 | Slichter |
| 2005/0009913 | A1 | 1/2005 | Mohr |
| 2007/0098697 | A1 | 5/2007 | Goodrich et al. |

(Continued)

OTHER PUBLICATIONS

Office Action for Canadian Application No. 3,025,799, Dated Dec. 9, 2024, 3 pages.

(Continued)

*Primary Examiner* — Dirk R Bass

(74) *Attorney, Agent, or Firm* — Lee & Hayes, P.C.

(57) ABSTRACT

Methods and compositions for the prevention or reduction of platelet transfusion associated complications are provided. The subject methods include modifying donor whole blood or platelets prior to transfusion to prevent or reduce alloimmune platelet refractoriness.

15 Claims, 14 Drawing Sheets

(56) References Cited

U.S. PATENT DOCUMENTS

| | | | |
|---|---|---|---|
| 2012/0093793 A1 | 4/2012 | Slichter |
| 2013/0131639 A1 | 5/2013 | Slichter |
| 2013/0288387 A1 | 10/2013 | Blancher et al. |
| 2019/0117694 A1 | 4/2019 | Slichter |

OTHER PUBLICATIONS

The Canadian Office Action mailed May 11, 2023 for Canadian patent application No. 3,025,799, a foreign counterpart of U.S. Appl. No. 16/303,578, 3 pages.
European Office Action mailed Aug. 25, 2021 for European Application No. 17803758.6, a foreign counterpart to U.S. Appl. No. 16/303,578, 9 pages.
Julmy, et al., "Transfusion Medicine and Hemotherapy", vol. 41, 2014, pp. 176-181.
Non Final Office Action dated Jul. 9, 2020 for U.S. Appl. No. 16/303,578, 17 pages.
Non Final Office Action for U.S. Appl. No. 16/303,578, mailed on Aug. 16, 2021,15 Pages.
Final Office Action for U.S. Appl. No. 16/303,578, mailed on Mar. 28, 2022, 16 Pages.
Final Office Action for U.S. Appl. No. 16/303,578, mailed on Apr. 13, 2021, 12 pages.
Zhu, et al., "Transfusion Medicine and Hemotherapy", vol. 41, 2014, pp. 189-196.
Asano, et al., "Treatment with riboflavin and ultraviolet light prevents alloimmunization to platelet transfusions and cardiac transplants," Transplantation, vol. 84, 2007, pp. 1174-1182.
Blundell, et al., "A prospective, randomized study of the use of platelet concentrates irradiated with ultraviolet-B light in patients with hematologic malignancy," Transfusion, vol. 36, No. 4, 1996, pp. 296-302.
Cardo, et al., "Pathogen inactivation of Trypanosoma cruzi in plasma and platelet concentrates using riboflavin and ultraviolet light" Transfus. Apher. Sci., vol. 37, No. 2, 2007, pp. 131-137.
Extended European Search Report Dated Dec. 2, 2019 for European Application No. 17803758.6, 10 pages.
Goodrich, et al., "The Mirasol PRT system for pathogen reduction of platelets and plasma: an overview of current status and future trends," Transfus. Apher. Sci., vol. 35, No. 1, 2006, pp. 5-17.
Imuflex WB-SP Blood Bag System, Terumo Transfusion Products, 5 pages, 2006, May be retrieved at<URL:https://www.terumobct.com/location/emea/Documents/IMUFLEX_WB_SP Sales Brocure,pdf>.
Mohr, et al., "A novel approach to pathogen reduction in platelet concentrates using short-wave ultraviolet light," Transfusion, vol. 49, No. 12, 2009, pp. 2612-2624.
Mundt, et al., "Chemical and Biological Mechanisms of Pathogen Reduction Technologies," Photochemistry and Photobiology, vol. 90, 2014, pp. 957-964.
Non Final Office Action dated Jul. 9, 2020 for U.S. Appl. No. 16/303,578, "Methods of Preventing Platelet Alloimmunization and Alloimmune Platelet Refractoriness and Induction of Tolerance in Transfused Recipients", Slichter, 17 pages.
Final Office Action Dated Sep. 16, 2019 for U.S. Appl. No. 15/167,923, 28 pages.
Office Action Dated Mar. 19, 2019 for U.S. Appl. No. 15/167,923, 25 pages.
Office Action dated Apr. 10, 2020 for U.S. Appl. No. 14/886,815, 29 pages.
Office Action dated Apr. 13, 2020 for U.S. Appl. No. 15/167,923, 32 pages.
Office Action for U.S. Appl. No. 16/303,578, mailed on Apr. 13, 2021, Slichter, "Methods of Preventing Platelet Alloimmunization and Alloimmune Platelet Refractoriness and Induction of Tolerance in Transfused Recipients", 12 pages.
Office Action dated Apr. 17, 2020 for U.S. Appl. No. 16/134,773, 32 pages.
Office Action Dated Jul. 30, 2019 for U.S. Appl. No. 14/886,815, 30 pages.
Picker, et al., "Effects of Mirasol PRT treatment on storage lesion development in plasma-stored apheresis-derived platelets compared to untreated and irradiated units," Transfusion, vol. 48, No. 8, 2008, pp. 1685-1692.
Reddy, et al., "Toxicity testing of a novel riboflavin-based technology for pathogen reduction and white blood cell inactivation," Transfus. Med. Rev., vol. 22, No. 2, 2008, pp. 133-153.
Reikvam, et al., "The Mirasol Pathogen Reduction Technology system and quality of platelets stored in platelet additive solution," Blood Transfusion, vol. 8, No. 3, 2010, pp. 186-192.
Seghatchian, et al., "Characteristics of the Theraflex UV-Platelets pathogen inactivation system—An update", Transfusion and Apheresis Science, vol. 46, No. 2, 2012, pp. 221-229.
Seltsam and Muller, et al., "UVC Irradiation for Pathogen Reduction of Platelet Conentrates and Plasma," Transfus Med. Hemother, vol. 38, No. 1, 2011, pp. 43-54.
Slichter, et al., "Leukocyte Reduction and Ultraviolet B Irradiation of Platelets to Prevent Alloimmunization and Refractoriness to Platelet Transfusions," The New England Journal of Medicine, vol. 337, 1997, pp. 1861-1869.
Slichter, et al., "Prevention of platelet alloimmunization in dogs with systemic cyclosporine and by UV-irradiation or cyclosporine-loading of donor platelets," Blood, vol. 69, No. 2, 1987, pp. 414-418.
Search Report and Written Opinion Dated Aug. 4, 2017 in PCT/US2017/035055, 9 pages.
Tynngard, et al., "The effect of gamma irradiation on the quality of aphresis platelets druing storage for 7 days," Transfusion, vol. 48, 2008, pp. 1669-1675.

Gating strategy for characterization of cells remaining in PRP and after filtration. All gates were set on canine whole blood.

Characterization of cells remaining in PRP and after filtration with Fenwal PLS-5A or Pall PL-1B filters.

Characterization of cells remaining after filtration with Fenwal PLS-5A or Pall PL-1B filters and centrifugation.

METHODS OF PREVENTING PLATELET ALLOIMMUNIZATION AND ALLOIMMUNE PLATELET REFRACTORINESS AND INDUCTION OF TOLERANCE IN TRANSFUSED RECIPIENTS

CROSS REFERENCE TO RELATED APPLICATIONS

This application is a U.S. National Phase Application of International Patent Application No. PCT/US2017/035055, filed May 30, 2017, which claims the benefit of priority to U.S. Provisional Patent Application No. 62/342,831, filed May 27, 2016, each of which is hereby incorporated by reference in its entirety.

STATEMENT OF GOVERNMENT SUPPORT

This invention was made with United States Government support under U.S. Army Medical Research and Materiel Command Grant No. 07328001, W81XWH-07-1-0578 and Department of Defense, and in part, by a grant provided by TERUMO® BCT, Lakewood, Colorado. The United States Government has certain rights in this invention.

FIELD

This invention is directed to methods of preventing transfusion related complications in recipients of donor blood or components thereof.

INTRODUCTION

Blood transfusion is the process of receiving blood products into one's circulation intravenously. Transfusions are used in a variety of medical conditions to replace lost components of the blood. Early transfusions used whole blood, but modern medical practice commonly uses only components of the blood, such as red blood cells, white blood cells, plasma, clotting factors, and platelets.

Transfusions of blood products is associated with complications, including immunologic transfusion reactions. One example of such an immunologic response is alloimmunization, an immune response generated in an individual or strain of one species in response to an alloantigen from a different individual or strain of the same species. Alloimmunization can result in the rejection of transfused or transplanted tissues, such as platelets, which leads to platelet refractoriness.

As a consequence, the platelet donor and recipient must be closely matched to avoid this immunological reaction. This process of matching can be a complicated and difficult procedure due to the complexity of the marker system that determines compatibility. Thus, the problem of alloimmunization of recipients against donor blood products is a major problem in transfusion medicine. The present invention provides solutions to these and other unmet needs in transfusion medicine.

SUMMARY

Described herein are methods and compositions for the prevention or reduction of alloimmune platelet refractoriness prior to transfusion by modifying donor platelets.

In a first aspect, the presently disclosed subject matter provides a method for reducing a recipient's risk of developing platelet alloimmunization upon receiving transfused donor platelets by filtering whole blood from a donor through a leukoreduction filter; performing pathogen reduction on the whole blood; and transfusing the resulting filtered and pathogen reduced whole blood into a recipient; thereby reducing the risk of the recipient developing platelet alloimmunization upon receiving transfused donor platelets. In some embodiments of this aspect, the pathogen reduction is performed by adding a photosensitizer to the whole blood; and irradiating the whole blood and photosensitizer with light. In some embodiments, this aspect comprises further preparing platelet rich plasma or a platelet concentrate from the filtered and pathogen reduced whole blood; and transfusing the resulting platelets into a recipient.

In an embodiment of this aspect, the leukoreduction filter can be a TERUMO IMUFLEX® WB-SP filter. In another embodiment of this aspect, the photosensitizer is riboflavin. In a further embodiment of this aspect, the light is UV light at a wavelength of between 290-370 nm. In various embodiments of this aspect, the donor whole blood or platelets can be from an antigenically mismatched donor, or else, the donor whole blood or platelets can be from an antigenically matched donor.

In a second aspect, the presently disclosed subject matter provides a method of preparing a toleragenic platelet composition that is substantially free or reduced of alloimmunizing cells by filtering whole blood from a donor to remove alloimmunizing cells; performing pathogen reduction on the whole blood; and recovering the filtered and pathogen reduced whole blood as the toleragenic platelet composition. In some embodiments of this aspect, the pathogen reduction is performed by adding a photosensitizer to the whole blood; and irradiating the whole blood and photosensitizer with light. In some embodiments, this aspect comprises further preparing platelet rich plasma or a platelet concentrate from the filtered and pathogen reduced whole blood.

In an embodiment of this aspect, the filtering is performed with a TERUMO IMUFLEX® WB-SP filter.

In a third aspect, the presently disclosed subject matter provides a method of preventing platelet refractoriness in a recipient receiving platelets from an antigenically mismatched donor by filtering whole blood from a donor through a leukoreduction filter; performing pathogen reduction on the whole blood; and transfusing the resulting filtered and pathogen reduced whole blood into the recipient; where the transfused platelets do not cause the recipient to develop platelet refractoriness, or delays or prevents the onset of platelet refractoriness. In some embodiments of this aspect, the pathogen reduction is performed by adding a photosensitizer to the whole blood; and irradiating the whole blood and photosensitizer with light. In some embodiments, this aspect comprises further preparing platelet rich plasma or a platelet concentrate from the filtered and pathogen reduced whole blood.

In an embodiment of this aspect, the leukoreduction filter can be a TERUMO IMUFLEX® WB-SP filter. In another embodiment of this aspect, the photosensitizer is riboflavin. In a further embodiment of this aspect, the light is UV light at a wavelength of between 290-370 nm.

In a fourth aspect, the presently disclosed subject matter provides a toleragenic platelet composition prepared by a process of filtering whole blood from a donor through a leukoreduction filter; and performing pathogen reduction on the whole blood. In some embodiments of this aspect, the pathogen reduction is performed by adding a photosensitizer to the whole blood; and irradiating the whole blood and photosensitizer with light. In some embodiments, this aspect comprises further preparing platelet rich plasma or a platelet concentrate from the filtered and pathogen reduced whole blood.

In an embodiment of this aspect, the leukoreduction filter can be a TERUMO IMUFLEX® WB-SP filter. In another embodiment of this aspect, the photosensitizer is riboflavin. In yet another embodiment of this aspect, the light is UV light at a wavelength of between 290-370 nm.

In a fifth aspect, the presently disclosed subject matter provides a toleragenic platelet composition capable of not producing an immune reaction in a recipient receiving the platelet composition.

In an embodiment of this aspect, the toleragenic platelet composition, when administered to a recipient, delays the development of immunization to the platelet composition in the recipient.

According to the subject embodiments, a dog platelet transfusion model can be employed, as a pre-clinical approach, to predict methods of modifying donor platelets whose results are transferable to humans. According to the subject embodiments, centrifuge leukoreduction (CL) can be combined with F-LR. As described further below, regardless of which of 4 types of described filters are used, in some aspects, 41/45 (91%) donors, e.g., dogs, accept donor platelets.

In some aspects, the subject methods are methods to prevent immunization from the residual WBCs that are not removed by F-LR. According to some aspects, the methods include assessing whether two methods of preventing transfusion-associated graft-versus-host disease (TAGVHD) might be effective when combined with F-LR; i.e., γ-irradiation (γ-I) or MIRASOL® pathogen reduction (MPR). The results of combining F-LR with γ-I or MPR to prevent alloimmune platelet refractoriness are described in greater detail below.

BRIEF DESCRIPTION OF THE DRAWINGS

FIG. 8A provides data relating to MPR. As shown, six of 7 recipients (86%) became refractory on treatment, and 1 of these refractory dogs developed post-transfusion purpura (PTP) after the fifth transfusion (her second refractory transfusion) when the dog's platelet count fell from 261,000/μl at the end of week 4 to 3,000/μl the next week. The dog had high levels of antibodies to both her donor's platelets (2.2×autologous control sera) and lymphocytes (1.7×autologous control sera). No auto antibodies were done as the dog's platelet count was too low. Of the 6 refractory dogs, 1 was not antibody tested. Among the 5 antibody tested dogs, 4 (80%) had antibodies to both lymphocytes and platelets, and 1 (20%) was antibody negative. The 1 non-refractory dog developed antibodies to both lymphocytes and platelets. There were no differences between means of pre- (47±5%) versus post-treatment (49±11%) autologous platelet recoveries (p=0.76), but there was a significant difference between pre- versus treated (21±7%) autologous platelet recoveries (p<0.001). FIG. 8B provides data relating to γ-I. As shown, all 5 recipients of γ-I platelets became platelet refractory with very poor responses even to their first donor transfusion. Four recipients (80%) developed antibodies to lymphocytes, 3 (60%) to platelets, and 1 was antibody negative. There were no differences between means of pre- (47±11%) versus post-treatment (49±7%) autologous platelet recoveries (p=0.66) nor between pre- versus treated (44±9%) autologous platelet recoveries (p=0.42).

FIG. 9A provides data relating to PLS-5A F-LR/MPR. As shown, 7 of 8 (88%) recipients accepted treated transfusions, 6 were antibody negative to both lymphocytes and platelets, 1 was not tested, and 1 refractory recipient was antibody positive to both lymphocytes and platelets. Five of 7 recipients (71%) who had accepted treated platelets subsequently became refractory to STD platelets, 1 was not tested. Among the 4 antibody tested dogs, 4 (100%) had lymphocyte antibodies, and none had platelet antibodies. Of 2 accepting recipients, 1 was antibody positive to both lymphocytes and platelets, and the other was antibody negative. There was no difference between means of pre- (53±12%) versus post-treatment (57±13%) autologous platelet recoveries (p=0.52), but there was a significant difference between pre- versus treated (33±9%) autologous platelet recoveries (p<0.001). FIG. 9B provides data relating to PL1-B F-LR/MPR. As shown, all 7 recipients accepted treated donor transfusions, none had antibodies to lymphocytes, and 1 (14%) had antibodies to platelets. On standard transfusions from their same donor, 4/7 (52%) recipients became refractory; 4 (100%) were positive to lymphocytes and 2 (50%) were positive to platelets. Of the 3 recipients who accepted STD platelets, 2 (66%) were positive to both lymphocytes and platelets, and 1 (33%) was antibody negative. There were no differences between means of pre- (46±9%) versus post-treatment (52±9%) autologous platelet recoveries (p=0.31), nor between pre- versus treated (43±7%) autologous platelet recoveries (p=0.56). FIG. 9C provides data relating to F-LR/MPR/γ-I. As shown, all 7 recipients accepted treated transfusions, none had antibodies to lymphocytes, and 1 (14%) had platelet antibodies. Five of the 7 (71%) became refractory to standard transfusions, 4 (80%) had antibodies to lymphocytes, 1 (20%) had antibodies to platelets, and 1 (20%) was antibody negative. Of the 2 who accepted STD transfusions, both were antibody negative. Four of the donors' platelets were PL1-B F-LR, and 3 were PLS-5A F-LR. There were no differences between means of pre- (47±6%) versus post-treatment (37%) autologous platelet recoveries (p=0.16), nor between pre- versus treated (42±4%) autologous platelet recoveries (p=0.15).

FIG. 10A provides data relating to MPR WB Followed By PL1-B F-LR of PRP. As shown, 2 of 5 recipients accepted treated transfusions and had no antibodies. Of the 3 refractory recipients, 2 (66%) had antibodies to lymphocytes, 1 (33%) had antibodies to platelets, and 1 was antibody negative. There were no differences between means of pre- (53±9%) versus post-treatment (55±8%) autologous platelet recoveries (p=0.83), but there was a significant difference in means of pre- and treated (27±13%) autologous platelet recoveries (p=0.002). FIG. 10B provides data relating to F-LR/WB followed by MPR/WB. As shown, all 10 recipients accepted treated donor platelets and had no evidence of antibodies. There were no differences between means of pre- (54±5%) and post-study (56±8%) autologous platelet recoveries (p=0.78), but there was a significant difference between pre- versus treated (46±7%) autologous platelet recoveries (p=0.03).

DETAILED DESCRIPTION

Figure 1:
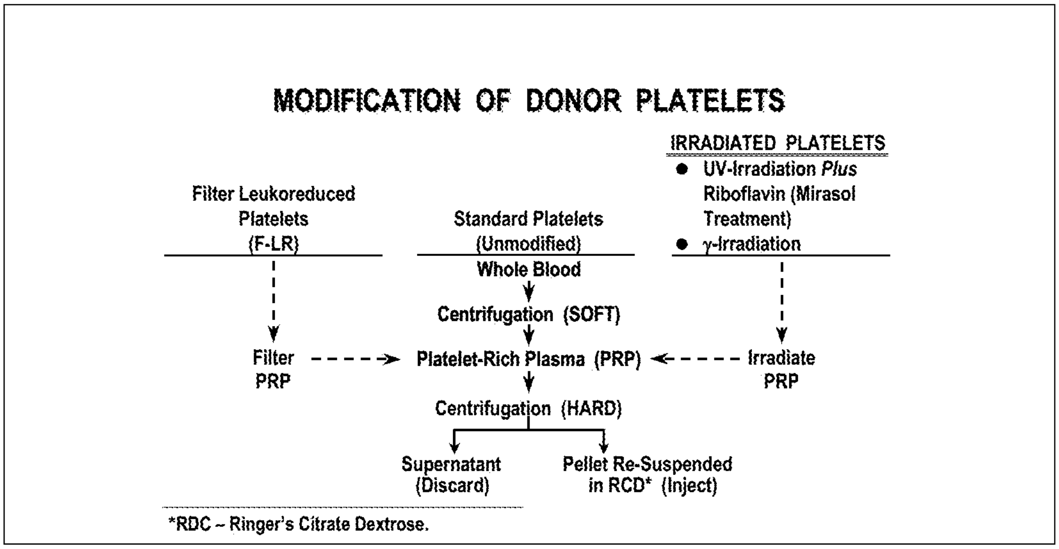
FIG. 1 shows steps to modify the donor dog's platelets prior to transfusion.

The presently disclosed subject matter generally relates methods and compositions for the prevention or reduction of platelet alloimmunization and refractoriness using leukoreduction and light treatment regimes, such as those used in pathogen reduction processes.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

Whole blood collected from volunteer donors for transfusion into recipients is typically separated into components: red blood cells, white blood cells, platelets, and plasma, using apheresis, centrifugation procedures, or other methods. Each of these separated blood components may be stored individually for later use and are used to treat a multiplicity of specific conditions and disease states. For example, the red blood cell component is used to treat anemia, the concentrated platelet component is used to prevent or control bleeding, and plasma is used frequently as a source of clotting factors for the treatment of congenital or acquired clotting factor deficiencies.

In cell separation procedures, there is usually some small percentage of other types of cells which are carried over into a separated blood component. When contaminating cells are carried over into a separated blood component in a high enough percentage to cause some undesired effect, the contaminating cells are considered to be undesirable. White blood cells, which may transmit infections such as HIV and CMV also cause other transfusion-related complications such as transfusion-associated Graft vs. Host Disease (TA-GVHD), alloimmunization and microchimerism.

Alloimmunization describes an immune response provoked in a transfused recipient by a donor alloantigen. Alloantigens include blood group substances (A, B, or AB) on erythrocytes and histocompatibility antigens expressed on white cells and platelets. An alloimmunizing cell as used herein is a cell which triggers an alloimmunization response against transfused platelets as described below.

Human Leukocyte Antigen (HLA) markers are found on the membranes of many different cell types, including white blood cells. HLA is the major histocompatibility complex (MHC) in humans, and contributes to the recognition of self v. non-self. Recognition by a transfusion recipient's immune system of differences in HLA antigens on the surface of transfused cells may be the first step in the rejection of transfused or transplanted tissues. Therefore, the phenomena of alloimmunization of recipients against HLA markers on donor blood is a major problem in transfusion medicine today. This issue arises in recipients of blood products due to the generation of antibodies against white blood cell HLA antigens in donor blood.

Platelets also express on their surface low levels of these HLA antigens. When a recipient of a whole blood or a blood component that contains donor white blood cells is transfused, the recipient may produce antibodies against the HLA antigens on the transfused donor's white blood cells. These antibodies may also lead to recognition and clearance of transfused platelets that carry this same marker. When this occurs, it becomes necessary to HLA match the platelet donor and recipient to assure that the recipient receiving the transfusion is able to maintain an adequate number of donor platelets in circulation. Finding an HLA-compatible donor is often a complicated, expensive and difficult procedure because of the complexity of the HLA system. Large numbers of potential platelet donors must be HLA-typed in order to have an available platelet donor registry that will contain compatible donors for most patients. In cases where recipients are very heavily transfused with blood or blood products from multiple donors and antibodies to many different HLA markers are generated, or where no suitable HLA-compatible platelet donor is available, death due to bleeding may occur.

One approach to preventing alloimmunization is to reduce the immunogenicity of the transfused blood products. As all transfused blood products are immunogenic and may eventually induce an immune response in most transfused recipients, any procedure that can prevent, reduce, or at least delay alloimmunization will be beneficial.

Since the immunization problem arises from the presence of white cells in the donated blood products, the elimination of white cells from these products would be expected to reduce the alloimmunization rates. Gamma irradiation of blood products, which kills the cells but does not remove them from the blood product to be transfused, has not been shown to be able to prevent alloimmunization. It is likely that this is due to the fact that the irradiated white cells are still present and capable of presenting antigens to the recipient's immune system. This hypothesis is supported by studies that have shown that gamma-irradiated lymphocytes are still able to stimulate other donor's lymphocytes in mixed lymphocyte cultures.

Filtration of white blood cells from blood or blood products to be transfused has been shown to be capable of reducing alloimmunization rates. This has been demonstrated based on an extensive clinical study referred to as the TRAP Trial. The TRAP Trial was conducted as a multi-institutional study between 1995 and 1997 and results were subsequently published in the NEJM in 1997 (Trial to Reduce Alloimmunization to Platelets Study Group. Leukocyte reduction and ultraviolet B irradiation of platelets to prevent alloimmunization and refractoriness to platelet transfusions. N Engl J Med. 1997; 337:1861-1869). The data from that study suggested that leukoreduction significantly decreased the likelihood of alloimmunization in patients from 45% for non-leukoreduced, untreated products to 17% to 18% for filter leukoreduced products. The remaining levels of alloimmunization that were observed in the TRAP Trial were believed to be due to residual white blood cells that were not removed by filtration. As a result of this work, platelet products have been filtered or centrifuged by a variety of methods to remove white blood cells. However, even the best white blood cell filters or centrifuge leukoreduction methods cannot remove 100% of the white blood cells, and those left behind are potentially able to stimulate antibody production against the HLA markers on the remaining cells. A decrease in the alloimmunization rate from 45% of patients receiving standard platelets to 17% to 18% is significant, but still leaves several tens of thousands of cases of alloimmunization occurring on an annual basis. Furthermore, when a subset analysis was done of the 36 patients in the TRAP Trial who had never had prior antigen exposure from transfusion or pregnancy and who received all of their transfusions as leukoreduced, the immunization rate was still 19%. The patients in the TRAP Trial all had Acute Myelogenous Leukemia and were undergoing potentially immunosuppressive induction chemotherapy. Thus, it is likely that the residual alloimmunization rates would have been much higher in an immunocompetent patient population.

In the same TRAP study, treatment of platelet products with ultraviolet B (UVB) light was also evaluated. In the case of UVB treatment, the results were equivalent to those obtained with filtration leukoreduction. The work was consistent with prior studies that showed that UVB treated platelet products possessed significantly reduced alloimmunization responses (Blundell et al. Transfusion 1996; 36: 296-302). This was believed to be due to changes in white cells induced by UVB that cause them to present their antigens and have those antigens processed differently from non-irradiated cells by the patient's immune system. The result is that antibody generation is significantly suppressed for UVB treated products. Although the results were positive, the UVB treatment described in the TRAP study was never implemented.

Photosensitizers, or compounds which absorb light of a defined wavelength and transfer the absorbed energy to an electron acceptor may be a solution to some of the above problems. Instead of physically removing contaminating white blood cells as leukoreduction procedures do, photosensitizers chemically inactivate the undesirable white cells without substantially damaging the desirable components of blood.

There are many photosensitizer compounds which are useful for inactivating undesirable cells and/or other infectious particles. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, anthroquinones and endogenous photosensitizers.

When illuminated with UV light, riboflavin, or 7, 8-dimethyl-10 ribityl isoalloxazine, an endogenous photosensitizer, has been shown to help reduce transfusion-related complications in a blood transfusion recipient. This is taught in U.S. Pat. No. 7,648,699.

In those instances where filtration of blood or a blood component to be transfused into a recipient does not remove enough of the white blood cells to prevent alloimmunity, it was discovered according to the subject embodiments that adding one or more additional treatments to inactivate the remaining white blood cells is surprisingly effective. Additional treatments may include the addition of a photosensitizer to the filter leukoreduced blood/blood component. The photosensitizer and filter leukoreduced blood/blood component may then be exposed to light for a sufficient amount of time to reduce the immunogenicity of the remaining white blood cells in the donor blood to such an extent that little or no immune response to the donor blood is generated by the recipient.

A of a number of leukoreduction methods can be used in the practice of the presently disclosed subject matter. Leukoreduction refers generally to any process which physically removes immunogenic cells, particularly, white blood cells (or leukocytes), from the blood or blood components supplied for blood transfusion. After the removal of the immunogenic cells or leukocytes, the blood product is said to be leukoreduced. Methods for performing leukoreduction include, but are not limited, to centrifugation and filtration. In performing centrifugation to produce leukoreduced platelets, differential centrifugation is performed to separate platelets from immunogenic cells such as WBCs. Centrifugation may result in the leukoreduction of a sample by at least 5%, 10%, 20%, 30%, 40%, 50%, 60%, 70%, 80%, 90%, or 100%, and all numbers in between, as compared to non-leukoreduced samples.

A leukoreduction filter is any filter which is capable of physically removing immunogenic cells, particularly, white blood cells (or leukocytes), from the blood or blood components supplied for blood transfusion using filtration methods. Leukoreduction filters are commercially available. Examples of leukoreduction filters include, but are not limited, to those made by FENWAL® Blood Technologies (e.g., PLS-5A filter), PALL® Corporation (e.g., PALL® PLF-1, PL-1B, LEUKOGUARD® RS, LEUKOTRAP® SC PL, LRF-10, PURECELL® LRF, PXL 8 and 12, PXLA, RCXL 1 and 2), among others. Filtration may result in the leukoreduction of a sample by at least 5%, 10%, 20%, 30%, 40%, 50%, 60%, 70%, 80%, 90%, or 100%, and all numbers in between, as compared to untreated samples.

A of a number of light or irradiation treatment methods can be used in the practice of the presently disclosed subject matter. The light source may be of many wavelengths, with wavelengths in the UV range being advantageous. Light treatment or irradiation can be performed with or without a photosensitizer as described below. In some aspects of the disclosed subject matter, the light treatment regime is one which is used in pathogen reduction processes using light or irradiation. Such pathogen reduction processes typically employ irradiation in the presence or absence of a photosensitizer to cross-link pathogenic cellular components such as nucleic acids.

Among the pathogen reduction methods that may be used in the practice of the present subject matter include, without limitation, those that rely on riboflavin and UV light (e.g., MIRASOL® Pathogen Reduction Technologies System from CardianBCT, Lakewood, CO); those that rely on psoralen and UV light (e.g., Cerus INTERCEPT Blood System, Concord, CA); and those that rely solely on UV-C light treatment (e.g., Seltsam and Muller, Transfus Med Hemother, 2011, 38: 43-54; Mohr et al., Transfusion, 2009, 49: 2612-24).

Photosensitizers useful in the presently disclosed subject matter include endogenous photosensitizers. The term "endogenous" means naturally found in a human or mammalian body, either as a result of synthesis by the body or because of ingestion as an essential foodstuff (e.g., vitamins) or formation of metabolites and/or byproducts in vivo. When endogenous photosensitizers are used, particularly when such photosensitizers are not inherently toxic or do not yield toxic photoproducts after photoradiation, no removal or purification step is required after decontamination, and the decontaminated product can be directly administered to a recipient in need of its therapeutic effect.

Examples of such endogenous photosensitizers which may be used in the presently disclosed subject matter are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavin adenine dinucleotide [FAD]) and alloxazine mononucleotide (also referred to as flavin mononucleotide [FMN] and riboflavine-5-phosphate). The term "alloxazine" includes isoalloxazines.

Use of endogenous isoalloxazines as a photosensitizer to pathogen reduce blood and blood components are described in U.S. Pat. Nos. 6,258,577 and 6,277,337 both issued to Goodrich et al.

According to various embodiments of the subject disclosure, the methods include both filtering whole blood (WB) from a donor and performing pathogen reduction, such as pathogen reduction including MIRASOL® pathogen reduction (MPR). In various embodiments, MIRASOL® pathogen reduction (MPR) is performed by adding a photosensitizer, e.g., riboflavin, to the whole blood and irradiating the whole blood and photosensitizer with light, e.g., UV light, e.g., UV light at a wavelength of between 290-370 nm, on the whole blood. In such embodiments of the disclosure, donor platelet acceptance rates can be 50% or more, such as 60% or more, such as 70% or more, such as 80% or more, such as 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more. Such acceptance rates can also range from 80% to 100%, such as 90% to 100%, such as 95% to 100%, each inclusive. As used herein, "inclusive" refers to a provided range including each of the listed numbers. Unless noted otherwise herein, all provided ranges are inclusive.

The subject methods can also include estimating donor platelets acceptance rates, e.g., the recipient acceptance of donor platelets of a toleragenic platelet composition, to be in any of the aforementioned ranges. Such an estimation produces an estimated recipient acceptance of donor platelets. Such estimated acceptance rates can be based on acceptance rates of whole blood in one or more, e.g., a plurality of, previously performed transfusions of whole blood, e.g., whole blood filtered through a leukoreduction filter and/or having had pathogen reduction performed on it.

Additionally, systems, devices, and methods associated with MPR which may be employed according to the subject embodiments include those described and referenced in: Goodrich R P, Edrich R A, LI J, Seghatchian J. The MIRASOL® PRT system for pathogen reduction of platelets and plasma: an overview of current status and future trends. Transfus Apher Sci 2006; 35:5-17; Asano H, Lee C Y, Fox-Talbot K, et al. Treatment with riboflavin and ultraviolet light prevents alloimmunization to platelet transfusions and cardiac transplants. Transplantation. 2007; 84:1174-82; Cardo L J, Salata J, Mendez J, et al. Pathogen inactivation of *Trypanosoma cruzi* in plasma and platelet concentrates using riboflavin and ultraviolet light. Transfus Apher Sci. 2007; 37:131-7; Picker S M, Steisel A, Gathof B S. Effects of MIRASOL® PRT treatment on storage lesion development in plasma-stored apheresis-derived platelets compared to untreated and irradiated units. Transfusion. 2008; 48:1685-92; Reddy H L, Dayan A D, Cavagnaro J, et al.

Toxicity testing of a novel riboflavin-based technology for pathogen reduction and white blood cell inactivation. Transfus Med Rev. 2008; 22:133-53, which are hereby incorporated by reference in its entirety for all purposes.

In various embodiments, the methods include the sequential steps of filtering whole blood from a donor through a leukoreduction filter and performing pathogen reduction comprising MIRASOL® pathogen reduction (MPR) on the whole blood. In various embodiments, the methods do not include irradiating the whole blood, such as performing pathogen reduction by γ-irradiating the whole blood.

Also, the subject methods include reducing the risk of the recipient developing platelet alloimmunization upon receiving transfused donor platelets. In various aspects, the methods include reducing the risk of the recipient developing platelet alloimmunization upon receiving transfused donor platelets by 75% or more, such as 80% or more, such as 85% or more, such as 90% or more, such as 91% or more, such as 92% or more, such as 93% or more, such as 94% or more, such as 95% or more, such as 96% or more, such as 97% or more, such as 98% or more, such as 99% or more, such as 99.5% or more.

Generally, whole blood is withdrawn from a donor and separated into components such as platelets, plasma and red blood cells, either manually by centrifugation procedures, or automatically. If separated automatically, such as by apheresis, an apheresis machine such as a TRIMA® apheresis machine (CaridianBCT, Inc., Lakewood, CO) can be used, or a whole blood separation machine such as an Atreus whole blood separation machine (CaridianBCT Inc., Lakewood, CO) can be used.

The non-immunogenic and toleragenic platelet compositions produced as a result of both filtration or centrifuge leukoreduction and irradiation of riboflavin with UV light may be used for tolerance induction. Toleragenic refers to the capacity of a composition to not generate an immunologic response to a given antigen that, under normal circumstances would likely induce cell-mediated or humoral immunity. An immunogenic reaction generally occurs at the earliest 10-14 days after platelet transfusion in a naïve recipient. Thus, a toleragenic platelet composition is one which does not produce an immunogenic reaction more than 10-14 days after platelet transfusion, preferably more than 3 weeks, more than 4 weeks, more than 5 weeks, more than 6 weeks, more than 7 weeks, or more than 8 or greater weeks after platelet transfusion. Tolerance is induced by administering transfusions, generally repeated transfusions, of the treated platelet composition to a recipient.

Platelet refractoriness occurs when a recipient fails to obtain a satisfactory response to two or more successive platelet transfusions. In clinical practice, there is usually little doubt when patients are failing to have satisfactory responses to a platelet transfusion, as indicated by no increase in platelet count on the day of or the day after a platelet transfusion.

To determine whether platelet refractoriness has occurred as a result of alloimmunity, platelet responses are measured in conjunction with antibody assays using donor lymphocytes or platelets as the target cell. Platelet responses are measured by determining pre- and post-transfusion platelet counts and calculating platelet increments, % platelet recovery, or corrected count increments. A recipient is considered platelet alloimmune refractory to the donor's platelets if the one-hour post-transfusion Corrected Count Increment, CCI is ≤7,500 (namely, 0-7,500 and all numbers in between) or the 24-hour post-transfusion CCI is ≤4,500 (namely, 0-4,500 and all numbers in between), along with a positive antibody assay against the donor's lymphocytes or platelets.

The subject embodiments include methods for reducing a recipient's risk of developing platelet alloimmunization upon receiving transfused donor platelets. Methods also include preparing a toleragenic platelet composition. The methods can include measuring one or more aspects of a sample and/or treating, such as by performing pathogen reduction and/or irradiation, on a sample prior to a transfusion.

The embodiments also include predicting that a treated, e.g., filtered, and/or pathogen reduced and/or irradiated sample, with or without riboflavin, will pose a lower risk, e.g., a lower risk of causing platelet alloimmunization, to a subject upon transfusion as compared, for example, to a control non-treated sample. As such, various aspects of the methods include providing, such as by generating, a predicted acceptance rate by predicting that a treated, e.g., pathogen reduced and/or irradiated sample, will have an acceptance rate of a particular amount, such as 70% or higher 75% or higher, 80% or higher, 85% or higher, 90% or higher, or 90% or higher, or any of the other acceptance rate values provided herein or higher, and as such, will pose a lower risk, e.g., a lower risk of causing platelet alloimmunization, to a subject upon transfusion as compared, for example, to a control non-treated sample. Based on the predicted acceptance rate, a treated sample can be transfused, stored for later transfusion, not transfused and/or discarded.

In some aspects of the embodiments, the subjects are immunosuppressed. In other aspects, the subjects are not immunosuppressed. As such, the subject's normal immune system operates throughout some of the various embodiments.

In some versions, aspects of the methods are performed using whole blood and not a fraction thereof, such as a sample of plasma or red blood cells or white blood cells. For example the methods include filtering whole blood from a donor through a leukoreduction filter; performing pathogen reduction on the whole blood by adding riboflavin to the whole blood and irradiating the whole blood and riboflavin with UV light; and transfusing the filtered and pathogen reduced whole blood.

Human Lymphocyte Antigen (HLA) alloimmunization to filter leukoreduced (F-LR) platelets occurs in about 18% of immunosuppressed thrombocytopenic hematology/oncology patients. According to some embodiments, in a platelet transfusion, such as a dog platelet transfusion model, other methods of preventing alloimmune platelet refractoriness are evaluated. In some aspects, methods to prevent alloimmunization in a dog model are transferable to a human.

As described in greater detail below, according to some aspects, donor/recipient pairs are dog lymphocyte antigen (DLA) incompatible (88% of the pairs). In some versions, recipient dogs are administered up to 8 weekly treated transfusions from a single donor (a highly immunogenic stimulus), or until platelet refractoriness. In some aspects, neither γ-irradiation (γ-I) nor MIRASOL® pathogen reduction (MPR) of donor platelets prevents alloimmune platelet refractoriness. For example, as provided herein, only 0/5 (0%) and 1/7 (17%) recipients accepted donor platelets, respectively. Combining γ-I with F-LR may in some aspects reduce acceptance of F-LR platelets; i.e., as described in accordance with studies below, acceptance of F-LR platelets occurred in 6/13 (46%) recipients versus 2/10 (20%) recipients given F-LR/γ-I platelets. In some embodiments, F-LR/MPR donor platelets are accepted by a number of recipients, such as 21/22 (95%) recipients ($p<0.001$ versus F-LR/γ-I recipients).

Furthermore, according to some aspects, a number of accepting recipients, such as 7/21 (33%) accepting recipients, demonstrate specific tolerance to 8 additional weekly non-treated donor transfusions. In addition, and as described below, in some aspects, platelet concentrates which are prepared from F-LR/MPR whole blood are also non-immunogenic. For example, as provided below, 10/10 (100%) recipients accepted donor platelets. In some aspects, a high number of recipients such, 31/32 (97%) recipients accept F-LR/MPR platelets, and do not develop antibodies to donor lymphocytes.

Also, in various embodiments, subjects which are recipients of treated blood or components thereof, e.g., platelets, in a transfusion do not have lymphocyte antibodies following the transfusion. Such treated blood is blood that is filtered, and then pathogen-reduced by MPR as is specifically described herein. As such, the subject methods include treating blood and/or components thereof, e.g., whole blood and/or platelets, such that when transfused, the blood does not result or substantially does not result in the production or presence of lymphocyte antibodies in a subject. For example, in various embodiments, a subject can have no lymphocyte antibodies after a transfusion of treated blood products. Also, as used herein, "substantially" means to a great or significant extent, such as almost fully or almost entirely. Furthermore, a small percentage of overall subjects to which treated blood, as provided herein, is transfused, e.g., 1, 2, 3, 4, 5, 6, 7, 8, 9, 10, 12, 15, 20, 25, 30 or more, etc., subjects can have lymphocyte antibodies. Of the subjects, 80% or more, 85% or more, 88% or more, 90% or more, 93% or more, 95% or more, 98% or more, or 99% or more, can be lymphocyte-antibody negative. In various embodiments, after transfusions are performed on a plurality of recipients, 80% or more of the recipients, such as 85% or more, 88% or more, 90% or more, 93% or more, 97% or more, 98% or more or 100% of the recipients are antibody negative to donor lymphocytes.

Furthermore, in some embodiments, subjects which are recipients of treated blood or components thereof, e.g., platelets, in a transfusion do not have any or substantially any platelet antibodies not associated with platelet refractoriness following the transfusion. Such treated blood is blood that is filtered, and then pathogen-reduced by MPR as is specifically described herein. As such, the subject methods include treating blood and/or components thereof, e.g., whole blood and/or platelets, such that when transfused, the blood does not result or substantially does not result in the production or presence of any or substantially any platelet antibodies not associated with platelet refractoriness in a subject. For example, in various embodiments, a subject can have no any or substantially any platelet antibodies not associated with platelet refractoriness after a transfusion of treated blood products. Furthermore, a small percentage of overall subjects to which treated blood, as provided herein, is transfused, e.g., 1, 2, 3, 4, 5, 6, 7, 8, 9, 10, 12, 15, 20, 25, 30 or more, etc., subjects can have platelet antibodies not associated with platelet refractoriness. Of the subjects, 80% or more, 85% or more, 88% or more, 90% or more, 93% or more, 95% or more, 98% or more, or 99% or more, can be negative as to any platelet antibodies not associated with platelet refractoriness. In some embodiments, after transfusions are performed on a plurality of recipients, 80% or more of the recipients, such as 85% or more, 88% or more, 90% or more, 93% or more, 97% or more, 98% or more or 100% of the recipients are antibody negative to donor platelets.

Utility

One of the biggest problems in the transfusion support of chronically-thrombocytopenic patients is alloimmunization to donor platelets. Contaminating white blood cells (WBCs), rather than platelets themselves, may represent a major immunogen in transfused platelets. To determine whether removal or inactivation of WBCs using filter leukoreduction (F-LR) or UV-B irradiation (UVB), respectively, for example as provided herein, could prevent platelet alloimmunization. Also, it could be difficult to quality control a C-LR process within routine blood center operations. As such, F-LR/C-LR is eliminated as a practical approach to preventing alloimmunization. The subject embodiments applied a platelet transfusion model, e.g., a dog model, as a pre-clinical approach, to predict methods of modifying donor platelets.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Experimental Design and Methods

The following experimental methods are used in the Examples that follow.

Experimental Design of the Dog Platelet Transfusion Studies

1) Perform baseline autologous radiolabeled platelet recovery and survival measurements in recipient dogs to ensure that their data is normal.
2) Select DLA, DRB mismatched and crossmatch negative random donor/recipient pairs.
3) Prepare platelets weekly from a single random donor.
4) Donor dog's platelets are unmodified (standard), filter-leukoreduced, γ-irradiated, UV-irradiated plus riboflavin (MIRASOL® pathogen reduction technology), or treatments are combined.
5) Donor dog's platelets, after modification, are radiochromium labeled prior to recipient transfusion.
6) Serial blood samples are drawn from the recipient to determine recovery and survival of the donor dog's radiolabeled platelets.
7) Recipient receives up to 8 weekly transfusions from their donor or until they become platelet refractory.
8) Primary Endpoint: Refractoriness is defined as <5% of the radiolabeled donor dog's platelets still circulating in the recipient at 24 hours post-transfusion after two sequential transfusions.
9) Autologous radiolabeled platelet recovery and survival measurements in the recipient dogs are repeated after donor platelet transfusions are completed to ensure that any refractoriness to the donor dog's platelets is due to alloimmunization rather than a change in the condition of the recipient dog that would not allow even autologous platelets to circulate normally.

Modification of the Donor's Platelets

The steps used to modify a donor dog's platelets prior to transfusion are shown in FIG. 1.

Lymphocyte Antigen (LA) Typing

Nucleotide sequence alignments for approximately 50 DLA-DRB alleles were available online. Since most sequence variations are located in second exons of class II genes, the amplification primer sequences for various DRB loci and alleles were selected from the conserved regions of 5' and 3' ends of exon 2. Oligo-nucleotide probes were selected from regions with sequence variation, and probes were designed to ensure uniform melting temperatures ($T_M$) and to enable uniform hybridization and wash conditions. The oligoprobes were poly(T) tailed and bound on nylon membranes (oligoblot). Following specific amplification, the individual amplicons were hybridized to a single oligoblot containing multiple probes defining various DLA-DRB alleles. Excess of unhybridized PCR products were removed in stringent washes, and the oligoblots were subjected to an immunological detection step. Positive reactions were visualized either as color precipitate or on X-ray film depending on the method of preference.

Platelet And WBC Antibody Testing

Antibody identification studies were performed baseline and on weekly blood samples drawn from the recipient dogs to detect IgM and IgG antibodies to donor platelets and WBCs. Serum samples were also tested against the recipients' autologous platelets and WBCs as negative controls. Antisera from alloimmune platelet refractory animals were pooled and run as a positive control against both autologous and donor platelets and WBCs.

A flow cytometric assay was used to detect anti-IgG or anti-IgM antibodies to donor platelets, B cells, and CD8 positive white cells. Platelets and WBCs were isolated from donor and recipient's whole blood, and these cells were added to a tissue culture plate. Platelets were adjusted to 300,000/well and WBCs to 35,000/well. Dog sera were added to the wells along with cell identification reagents, followed by FITC-labeled anti-dog IgG and IgM reagents. Cells were incubated with the reagents, washed, staining buffer was added, and mean fluorescence of platelets and lymphocytes were detected using the FACScan. Results were considered positive for recipient antibodies against the donor's platelets or WBCs if the test sera were times the donor's autologous control sera tested with the same cells.

WBC Identification

Figure 2:
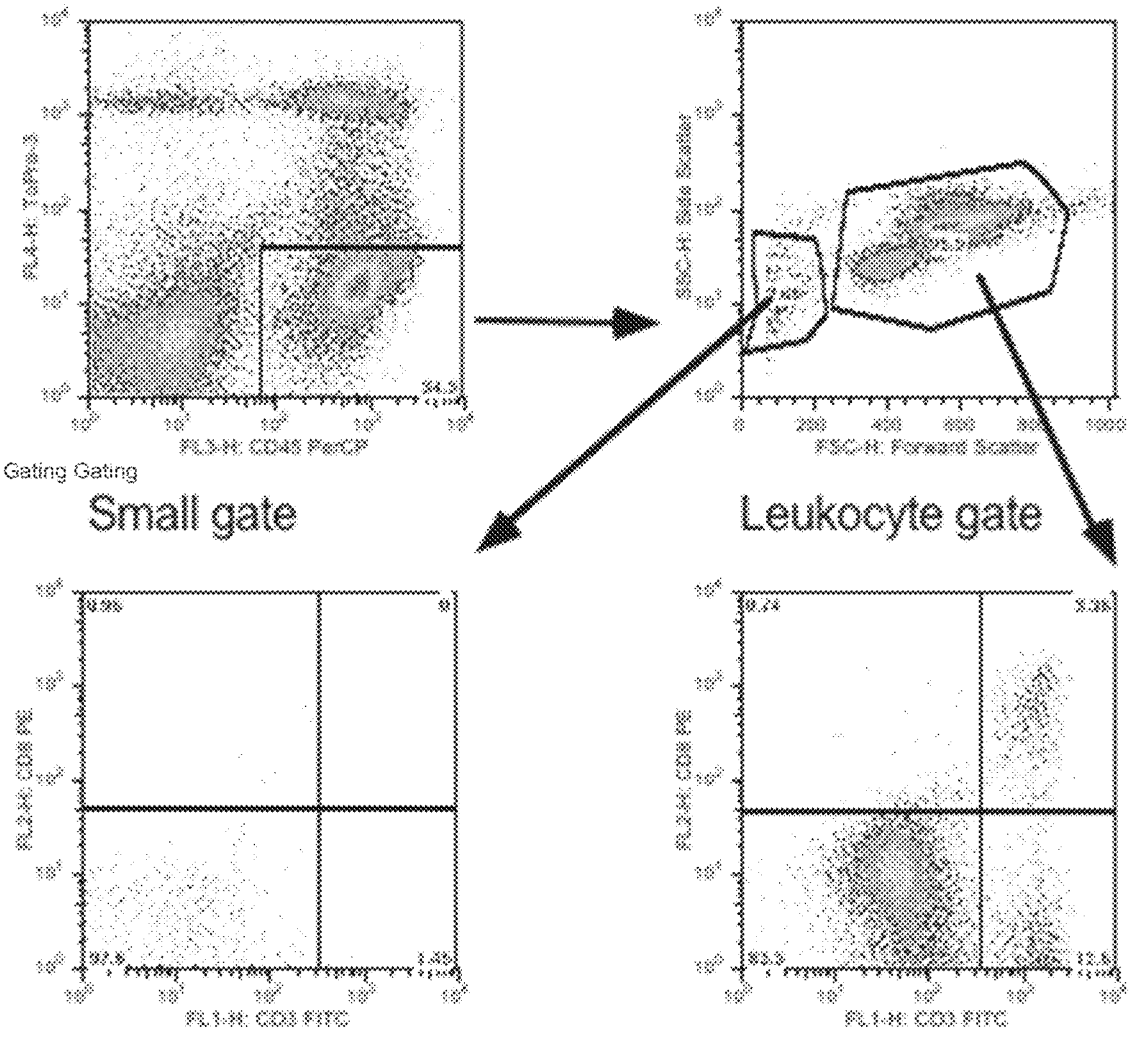
FIG. 2 shows the gating strategy for characterization of cells remaining in PRP and after filtration.

WBC identification was performed using a panel of anti-canine antibodies and a BD Facscalibur flow cytometer to detect the cell types and CD45 positive microparticles after filtration as compared to whole blood preparations. Briefly, the blood was processed and filtered using the same method used for transfusions. A whole blood sample was used as a reference sample, a platelet-rich-plasma (PRP) sample as another reference, and then the processed and filtered PRP samples were analyzed. The panel used to detect CD45 positive and topro negative (live) cells and microparticles was as follows: DM5 (granulocytes), B cell, class II, CD4, CD14, CD34, CD3, CD8, and isotype (to rule out nonspecific binding). In this way, any differences detected by this panel between the filters studied could be evaluated. The PRP was passed through a FENWAL® PLS-5A or PALL® PL-1B filter according to the method described above (FIG. 1). The filtrate was analyzed for the percentage and number of leukocytes that remained (FIG. 2).

Example 2: Effectiveness of Different Leukoreduction Methods

This example provides methods of modifying a donor dog's platelets prior to transfusion in a dog platelet transfusion model that would prevent alloimmune platelet refractoriness. In some aspects, methods of preventing platelet alloimmunization in a dog model could be successfully transferred to patients. Specifically, in some aspects, UV-B irradiation that was 45% successful in preventing alloimmunization in the dog was 81% successful in patients in the largest prevention of platelet alloimmunization trial ever conducted in patients (TRAP Trial). (See Slichter S J, Deeg H J, Kennedy M S. Prevention of platelet alloimmunization in dogs with systemic cyclosporine and by UV-irradiation or cyclosporine-loading of donor platelets. Blood 1987; 69(2): 414-418; The Trial To Reduce Alloimmunization To Platelets Study Group. Leukocyte reduction and ultraviolet B irradiation of platelets to prevent alloimmunization and refractoriness to platelet transfusions. N Engl J Med 1997; 337:1861-1869.) The fact that UV-B irradiation was even more successful in patients than in the dog is probably because the dogs had a normal immune system while being transfused versus a compromised immune system in the study patients who were receiving induction chemotherapy for acute myelogenous leukemia (AML). Therefore, any beneficial approach in the dog is likely to be even more successful in cancer patients receiving chemotherapy or stem cell transplants. These patients, who often receive prolonged platelet therapy, would benefit the most from methods to prevent alloimmunization.

Studies in a dog model have been performed suggesting that just a quantitative reduction in the number of residual white blood cells (WBCs) was not sufficient to prevent alloimmunization. Transfused WBCs contain antigen presenting cells (APCs) that present donor antigens to the recipient's immune system leading to alloimmunization. In fact, different methods of leukoreduction using centrifugation (C-LR) versus filtration (F-LR) that both produce the same levels of leukoreduction from $10^6$ WBCs/transfusion without leukoreduction to $10^4$ WBCs/transfusion with either method of leukoreduction produce different transfusion outcomes (Table 1). Even different filters produced different results.

TABLE 1

EFFECTS OF DIFFERENT METHODS OF LEUKOREDUCTION ON ACCEPTANCE OF DONOR PLATELETS

| Platelet Modification | ACCEPTANCE RATES # Donor's Accepted*/ # Recipients (%) | |
|---|---|---|
| None (Standard) | 1/7 | (14%) |
| Single Modification: | | |
| Centrifuge Leukoreduction (C-LR) | 3/21 | (14%) |
| Filter Leukoreductiond (F-LR) | | |
| Pall PLF-1 Filter | 4/13 | (31%) |
| Pall PL1-B Filter | 2/7 | (29%) |
| Fenwal PLS-5A | 4/6 | (66%) |

*Donor platelets accepted for 8 weeks.

As can be seen from Table 1, varying degrees of acceptance are obtained when different methods of leukoreduction are used, ranging from centrifuge leukoreduction (C-LR), which when used alone gives no better rate of acceptance than no treatment (14%). The FENWAL® PLS-5A filter gave the highest rate of acceptance at 66%.

It was then assessed as to whether combining different methods of preventing alloimmunization would increase donor platelet acceptance rates. Combining UV-B irradiation with C-LR gave acceptance rates of 55% compared to acceptance rates of 71% when UV-B was combined with F-LR. Based on acceptance rates for a single modification (C-R=14%, PALL® PLF-1 F-LR=31%, and UV-B irradiation=45%), combinations of LR with UV-B irradiation were additive in the results achieved (Table 2).

TABLE 2

DONOR PLATELETS

| | # Donors Accepted*/ # Recipients (%) | |
|---|---|---|
| C-LR plus UV-B | 6/11 | (55%) |
| F-LR** plus UV-B | 10/14 | (71%) |

*Donors accepted for 8 weeks.
**Pall PLF-1 filter.

Surprisingly, when C-LR was combined with two of the filters tested (PALL® 's PLF-1 and FENWAL® 's PLS-5A), donor acceptance rates were 95% to 100% versus only 50% with PALL® 's PL1-B filter (Table 3). The results with the first two filters (PALL® 's PLF-1 and FENWAL® 's PLS-5A) were synergistic rather than additive as obtained with the last filter.

TABLE 3

EFFECTS OF COMBINING F-LR WITH C-LR ON ACCEPTANCE OF DONOR PLATELETS

| Filter | F-LR # Donors Accepted**/ # Recipients (%) | | F-LR/C-LR* # Donors Accepted**/ # Recipients (%) | | |
|---|---|---|---|---|---|
| Pall | | | | | |
| PLF-1 | 4/13 | (31%) | 18/19 | (95%) | p = 0.007 (PLF-1 vs PL1B) |
| PL1B | 2/7 | (29%) | 6/12 | (50%) | |
| Fenwal | | | | | p = 0.02 (PL1B vs PLS-5A) |
| PLS-5A | 4/6 | (66%) | 10/10 | (100%) | |

*Residual WBCs all < 3 × $10^3$ (Lower limit of detection of the assay).
** Donor platelets accepted for 8 weeks.

The results shown in Table 3 are consistent with the idea that F-LR with PALL® 's PLF-1 and FENWAL©'s PLS-5A must remove different types of WBCs than does C-LR. Therefore, combining F-LR with C-LR gives almost complete prevention of alloimmune platelet refractoriness. Furthermore, although both the PLF-1 and PL1-B filters were made by PALL® and they produced the same amount of leukoreduction, they must be removing and/or leaving different types of WBCs because C-LR does not produce the same results when combined with the PLF-1 filter (95% donor acceptance rates) versus the PL1-B filter (50% donor acceptance rates).

It was then assessed as to whether the acceptance rates of the PL1-B filter could be improved by combining F-LR/C-LR with either UV-B irradiation or γ-irradiation (Table 4). Unexpectedly, adding UV-B irradiation to F-LR/C-LR did not improve the results while adding γ-irradiation was 100% successful.

TABLE 4

ADDITIONAL MODIFICATIONS OF PL1-B FILTERED, CENTRIFUGED LEUKOREDUCED PLATELETS

| Platelet Modification | ACCEPTANCE RATES # Donors Accepted*/ # Recipients (%) | |
|---|---|---|
| PL1-B (F-LR/C-LR) | 6/12 | (50%) |
| PL1-B (F-LR/C-LR/UV-B irradiated) | 3/8 | (38%) |
| PL1-B (F-LR/C-LR/γ-irradiated) | 7/7 | (100%) |

*Donor platelets accepted for 8 weeks.

Example 3: WBC Identification

This Example describes experiments designed to characterize the WBCs that are removed and those that remain after F-LR and combined F-LR/C-LR procedures using monoclonal antibodies specific for canine WBCs.

The WBC identification method using FACS as described in Example 1 was employed for these studies.

Figure 3:
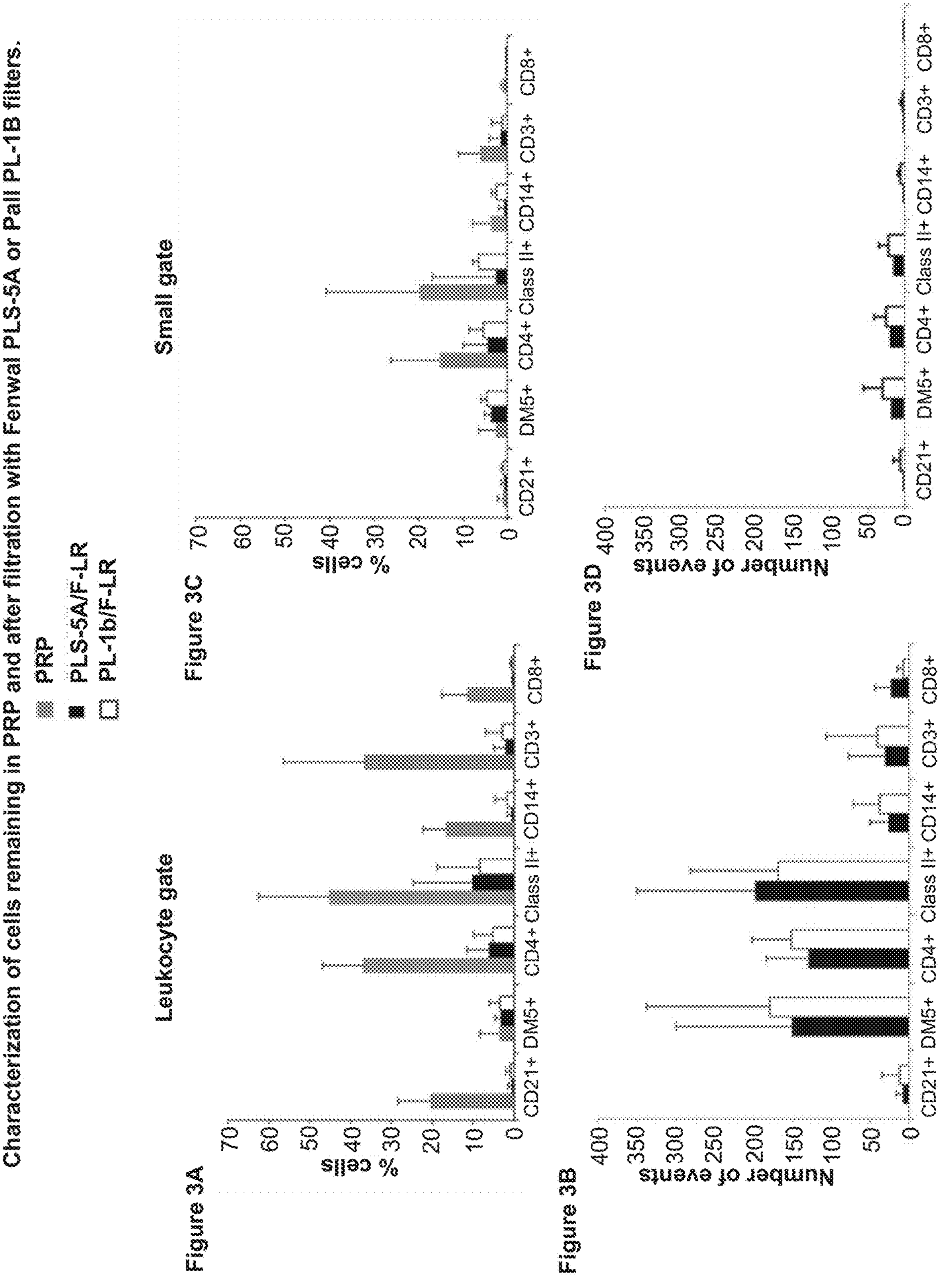
FIGS. 3A-3D shows a characterization of cells remaining in platelet-rich-plasma (PRP) and after filtration with FENWAL® PLS-5A or PALL® PL-1B filters.

As expected, the PRP was enriched for lymphocytes for example, B cells ($CD21^+$), T cells ($CD3^+$) and DLA Class II positive (CII+) cells (FIG. 3A). As canine granulocytes, monocytes and T cells express CD4; in the subject analysis CD4 positive cells are a mixture of all these cell types. Both FENWAL® PLS-5A and PALL® PL-1B filters removed most of the lymphocytes with the percentage of $CD8^+$ T cells and B cells in the leukocyte gate below 1% of the total $CD45^+$ cells (FIG. 3A). The analysis of the number of events showed that most of the cells remaining were granulocytes ($DM5^+$ cells) and CII+ cells (FIG. 3B). The percentage of cells and number of events in the low forward and size scatter gate (small gate; see FIG. 2) was also evaluated. This gate could consist of fragments of cells generated by the filters or microparticles. As in the leukocyte gate, the remaining cells were mostly $CII^+$ cells and granulocytes (FIGS. 3C, 3D). Further studies are needed to verify the properties of cells/particles within the small gate.

Figure 4:
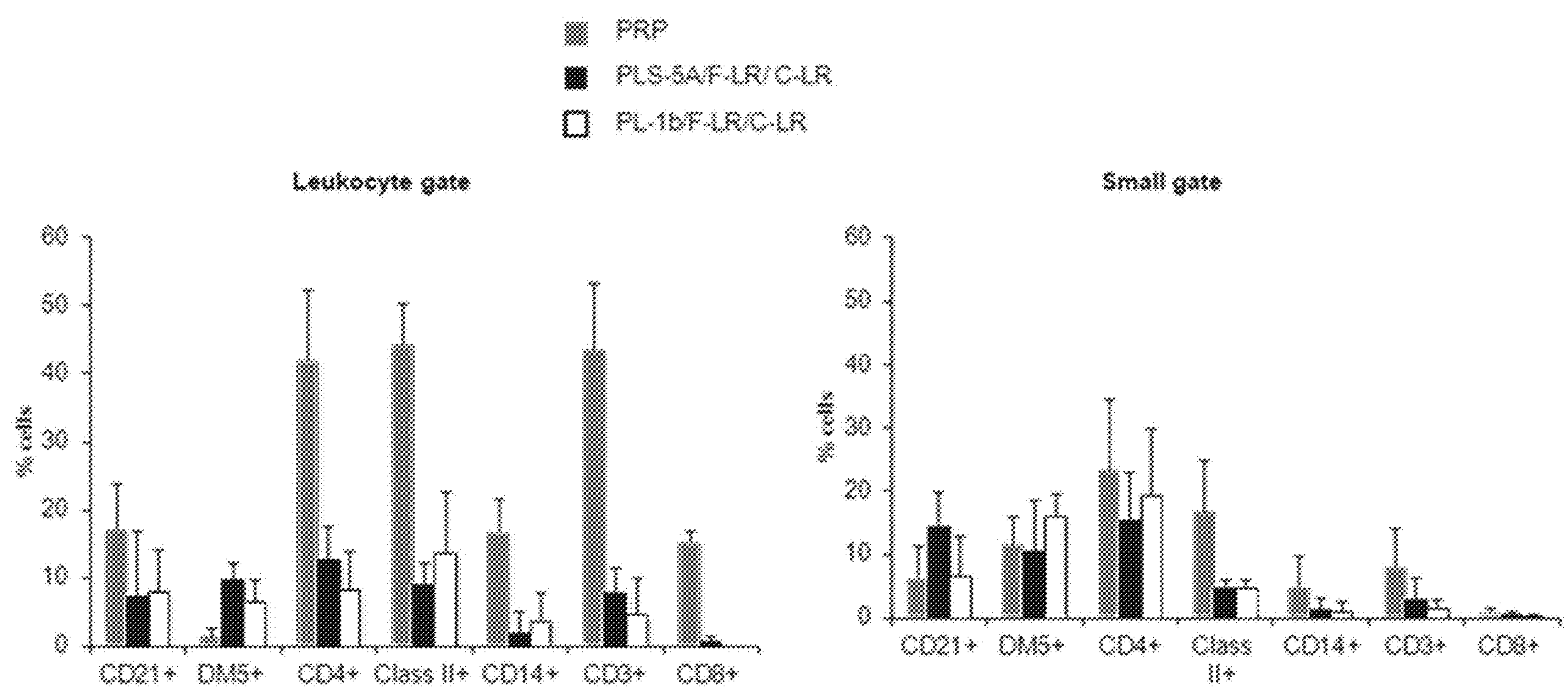
FIG. 4 shows a characterization of cells remaining after filtration with FENWAL® PLS-5A or PALL® PL-1B filters and centrifugation.

To investigate whether combined F-LR/C-LR removed and/or left different types of WBCs, cells were analyzed and left in the supernatant after filtration and low speed centrifugation. Surprisingly, after filtration followed by centrifugation (F-LR/C-LR), the remaining populations of cells were similar to F-LR alone except there was a slight enrichment of $CD21^+$ cells in the small gate (FIG. 4). This difference did not reach statistical significance.

Our results indicate that both FENWAL® PLS-5A and PALL® PL-1B filters remove 90% of leukocytes from PRP. The residual cells and fragments and/or microparticles after F-LR are mostly granulocytes and $CII^+$ cells. No difference in remaining cell populations between F-LR and F-LR/C-LR was detected.

Example 4: Modified Platelet Transfusion Experiments to Prevent Platelet Alloimmunization Following the results obtained with γ-irradiation, combined with PL1-B F-LR/C-LR in other prior studies (Example 2; Table 4), the effects of γ-irradiation alone or when combined with F-LR were then evaluated. F-LR and γ-irradiation are both processes that are routinely performed by blood centers.

In Table 5, it was first evaluated whether γ-irradiation alone could prevent alloimmune platelet refractoriness.

TABLE 5

| SINGLE PLATELET MODIFICATIONS | # Donors Accepted*/ # Recipients (%) | |
|---|---|---|
| None (Standard) | 1/7 | (14%) |
| Filtration: | | |
| Pall PL-1B Filter | 2/7 | (29%) |
| Fenwal PLS-5A Filter | 4/6 | (66%) |
| γ-Irradiation | 0/5 | (0%) |
| Mirasol Treatment | 1/7 | (14%) |

*Donor transfusions accepted for 8 weeks.

Figure 5:
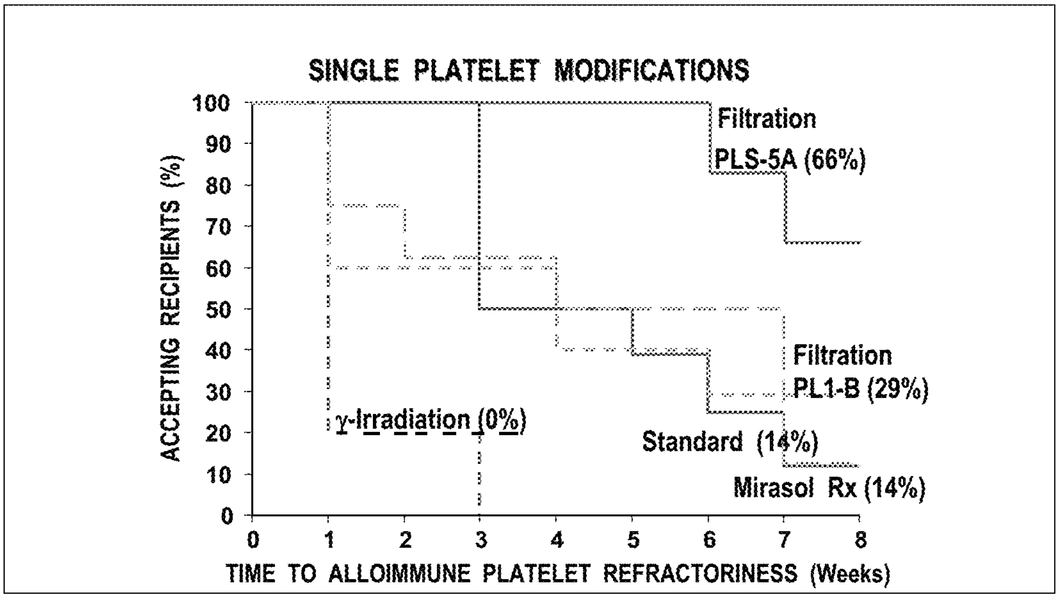
FIG. 5 shows time to alloimmune platelet refractoriness using single platelet modifications.

None of the 5 dogs given γ-irradiated donor platelets accepted these platelets, and the time to develop platelet refractoriness was even shorter than the time required for recipients to become refractory to standard (unmodified) donor platelets (FIG. 5).

Figure 6:
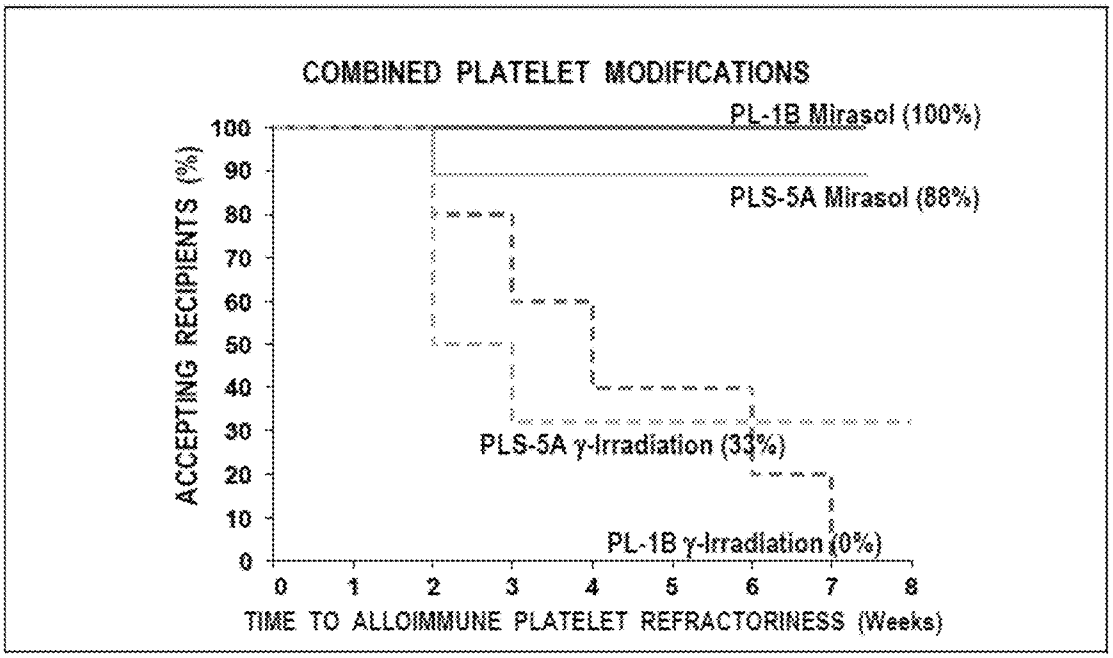
FIG. 6 shows time to alloimmune platelet refractoriness using combined platelet modifications.

It was then determined whether γ-irradiation combined with F-LR would improve the results achieved with F-LR alone. Adding γ-irradiation not only did not improve the acceptance of F-LR donor platelets (Table 6) or time to platelet refractoriness (FIG. 6), γ-irradiation may actually have reduced the effectiveness of F-LR using both the PALL® PL1-B and FENWAL® PLS-5A filters.

TABLE 6

COMBINED PLATELET MODIFICATIONS: FILTER LEUKOREDUCTION PLUS γ-IRRADIATION OR MIRASOL TREATMENT

| Filtration | γ-IRRADIATION # Donors Accepted*/ # Recipients (%) | | MIRASOL TREATMENT # Donors Accepted*/ # Recipients (%) | |
|---|---|---|---|---|
| Pall PL1-B** | 0/5 | (0%) | 7/7 | (100%) |
| Fenwal PLS-5A*** | 2/6 | (33%) | 7/8 | (88%) |
| Total | 2/11 | (18%) | 14/15 | (93%) |

p = 0.005

*Donor transfusions accepted for 8 weeks.
**PL1-B Only—2/7 (29%).
***PLS-5A Only—4/6 (66%).

Example 5: Combination of UV Light Treatment and Filtration

This Example provides experiments to determine whether a pathogen-reduction technology could prevent alloimmune platelet refractoriness in the dog model. The technology involves adding riboflavin to the platelets followed by UV-irradiation (MIRASOL® treatment). This process prevents replication of DNA and RNA in bacteria, viruses, and WBCs suggesting that it might prevent alloimmunization due to contaminating WBCs in the transfused platelets.

Treating the donor's platelets with MIRASOL® did not prevent platelet refractoriness, and the percentage of accepting recipients and time to refractoriness was the same as standard (unmodified) platelet transfusions (Table 5 and FIG. 5). In contrast, when MIRASOL® treatment was combined with either the PL1-B or PLS-5A filters, acceptance rates were 100% and 88%, respectively (Table 6 and FIG. 6). Using γ-irradiation combined with F-LR was effective at preventing alloimmune platelet refractoriness in only 2/11 (18%) of dogs compared to 14/15 (93%) of dogs who received MIRASOL® treated plus F-LR platelets (p=0.005).

In these experiments, antibody results correlated with platelet transfusion results 65% of the time for antibody tests against platelets and 67% of the time for antibody tests against WBCs; i.e., the assays were positive when the recipient developed refractoriness to donor platelets or antibodies were not detected when donor platelets were accepted for 8 weeks. The biggest problem with the antibody assays was failure to detect antibodies when the dog was platelet refractory; i.e., 30% of the recipients were negative for both platelet and WBC antibodies when the dog was platelet refractory. In contrast, antibodies were detected in only 5% and 2% of platelet and WBC antibody tests when the recipient did not become refractory to donor platelets. The failure to detect antibodies in 30% of the recipients who were refractory to donor platelets emphasizes the relevance of using refractoriness to donor platelets as the primary endpoint of the studies. Clinicians are much more interested in how well patients respond to platelet transfusions rather than their antibody status. As autologous radiolabeled platelet recovery and survival measurements at the end of the donor platelet transfusion experiments were all unchanged from baseline values, refractoriness to donor platelets in the studies was secondary to alloimmunization, even in the absence of positive antibody tests.

Example 6: Treatment of Whole Blood Samples by Filtration Leukoreduction and Pathogen Reduction

Background

The largest transfusion (tx) trial to evaluate methods of preventing platelet (plt) alloimmunization (TRAP Trial; NEJM 1997; 337:1861) demonstrated residual alloimmunization rates of 17% to 21% in AML patients undergoing induction chemotherapy despite receiving either filter-leukoreduced (F-LR) or UV-B irradiated (UV-BI) blood products, respectively. The pre-clinical dog platelet transfusion studies, the basis for testing UV-BI in the TRAP Trial, demonstrated this model was able to predict patient results; i.e., prevention of alloimmunization was 45% in the dog but 79% in patients. The greater effectiveness in patients was probably because they had chemotherapy-induced immunosuppression compared to the immunocompetent dogs. The dog platelet transfusion studies have focused on evaluating F-LR to remove antigen-presenting WBCs (APCs) or pathogen-reduction (PRT) (MIRASOL® treatment) to inactivate APCs.

Methods

For patients, platelets are obtained using either apheresis procedures or as platelet concentrates prepared from whole blood (WB). To re-duplicate these types of platelets in the dog model, platelet-rich-plasma (PRP) was prepared from WB which would be equivalent to non-leukoreduced apheresis platelets. The PRP was then either unmodified, F-LR, PRT, or the treatments were combined. Because the success rates were very poor with the single treatments of PRP (see Table 7), the WB studies evaluated only combined F-LR and PRT treatments. In clinical practice, the treated WB would then be used to prepare a platelet concentrate. The WB studies assessed either PRT of the WB followed by F-LR of PRP made from the WB or, conversely, F-LR of the WB using a platelet-sparing filter (TERUMO IMUFLEX® WB-SP) followed by PRT of the WB and then preparation of PRP. After completion of all treatments, PRP from each study was centrifuged to prepare a platelet concentrate, the platelets were radiolabeled with $^{51}Cr$, injected into a recipient, and samples were drawn from the recipient to determine recovery and survival of the donor's platelets. Donor (dnr) and recipient pairs were selected to be DLA-DRB incompatible and crossmatch-negative. Eight weekly donor platelet transfusions were given to the same recipient or until the recipient became refractory to the donor's platelets defined as ≤5% of the donor's platelets still circulating in the recipient at 24-hours post-transfusion following 2 sequential transfusions.

Results

Table 7 shows the percent of recipients who accepted 8 weeks of donor platelets and the total number of donor platelets and WBC injected. Using either filter, there was equal reduction in WBCs to $10^5$/transfusion. Acceptance of unmodified donor platelets was 1/7 recipients (14%), PRT 1/8 recipients (13%), PL1-B filter 1/5 recipients (20%), and PLS-5A filter 4/6 recipients (66%). None of these differences were statistically significant. In contrast, combining F-LR of the PRP followed by PRT of the PRP was effective in 21/22 recipients (95%), regardless of the filter used. WB studies showed donor platelets were accepted by 2/5 recipients (40%) when WB was first treated with PRT followed by F-LR of the PRP made from the WB. Conversely, if the WB was first F-LR followed by PRT of the WB, 5/6 (83%) accepted donor platelets.

TABLE 7

| Treatment | # Dnrs Accepted/ # Recipients (%) | Tx (#) | DONOR CELLS INJECTED | |
|---|---|---|---|---|
| | | | Total Plts | Total WBCs |
| None | 1/7 (14%) | 138 | $1.7 \times 10^9 \pm 8 \times 10^8$ | $1.2 \times 10^7 \pm 2.3 \times 10^6$ |
| PRP Treatment: | | | | |
| F-LR: | | | | |
| PALL ® PL1-B filter | 1/5 (20%) | 57 | $1.7 \times 10^9 \pm 4.5 \times 10^8$ | $6.0 \times 10^5 \pm 3.0 \times 10^4$ |
| FENWAL ® PLS-5A filter | 4/6 (66%) | 53 | $1.04 \times 10^9 \pm 5.0 \times 10^8$ | $3.6 \times 10^5 \pm 5.6 \times 10^4$ |
| PRT | 1/8 (13%) | 47 | $1.7 \times 10^9 \pm 1.8 \times 10^8$ | $1.6 \times 10^7 \pm 5 \times 10^6$ |
| F-LR Followed by PRT: | | | | |
| PALL ® PL1-B filter | 11/11 (100%) | 88 | $1.7 \times 10^9 \pm 4.7 \times 10^8$ | $8.2 \times 10^5 \pm 4.5 \times 10^4$ |
| FENWAL ® PLS-5A filter | 10/11 (91%) | 87 | $8.6 \times 10^8 \pm 3.7 \times 10^7$ | $1.7 \times 10^5 \pm 2.5 \times 10^4$ |
| TOTAL | 21/22 (95%) | | | |
| WB Treatment: | | | | |
| PRT of WB followed by PL1-B filtration of PRP | 2/5 (40%) | 35 | $1.1 \times 10^9 \pm 7.7 \times 10^7$ | $3.7 \times 10^5 \pm 4.5 \times 10^4$ |
| Filtration of WB with TERUMO IMUFLEX ® WB-SP filter followed by PRT of WB | 5/6 (83%) | 46 | $1.0 \times 10^9 \pm 1.8 \times 10^8$ | $7.0 \times 10^5 \pm 9.5 \times 10^4$ |

Data are given as average ± 1 S.D.

Conclusions

F-LR of PRP or WB followed by PRT of the same PRP or WB is highly-effective in preventing alloimmune platelet refractoriness in the dog platelet transfusion model. These data suggest that most of the APCs must be removed by filtration before PRT can eliminate the activity of any residual APCs. Based on the high rate of success of this combined approach in the immunocompetent dog model, similar results should be achieved in patients, even those who are not immunocompetent as were the AML patients receiving chemotherapy in the TRAP Trial.

While this example has shown the use of filter treatment followed by PRT (i.e., irradiation in the presence of a photosensitizer), one of skill in the art will recognize that in certain embodiments, these steps can be performed in reverse order in the practice of the present invention.

Example 7: Leukofiltration Plus Pathogen Reduction to Prevent Alloimmune Platelet Refractoriness

Introduction

Alloimmunization to filter leukoreduced (F-LR) platelets still occurs in 18% of hematology/oncology patients. In a dog platelet transfusion model, other methods of preventing alloimmune platelet refractoriness were evaluated that would be adaptable to routine blood center operations. In some aspects, results from a dog model are transferable to man.

In a dog platelet transfusion model, UV-B irradiation, filter-leukoreduction (F-LR) and centrifuge leukoreduction (C-LR) were previously evaluated either alone or in combination as methods of treating donor platelets to prevent alloimmune platelet refractoriness. (1-3) UV-B irradiation, based on the dog data, and F-LR were subsequently assessed in the Trial to Prevent Alloimmunization To Platelets (TRAP Trial), and they were 79% and 82% successful, respectively, in preventing alloimmunization in patients. (4) However, these approaches were only 45% and 29% to 66% (depending on the filter used) successful, respectively, in preventing alloimmune platelet refractoriness in the dog model. The differences in efficacy are likely related to the immunocompetence of the two groups; i.e., the transfused patients were undergoing induction chemotherapy for acute myelogenous leukemia and were likely immunosuppressed compared to the normal immune systems of the dogs. Two conclusions were formulated: 1) the dog may be a very relevant preclinical model to identify methods of preventing alloimmunization in patients; and 2) a highly-successful platelet transfusion approach in the dog may even be effective in non-immunosuppressed patients; e.g., those with myelodysplasia or aplastic anemia.

Combining centrifuge leukoreduction (CL) with F-LR, regardless of which of 4 filters were used, $^{41}/_{45}$ dogs (91%) accepted donor platelets. (3) These data suggest that more than one type of WBC is associated with alloimmunization, some being removed by filtration and others by centrifugation. (5) However, it would be very difficult to quality control a C-LR process within blood center operations. Therefore, assessing additional methods of preventing alloimmune platelet refractoriness in a dog model was continued.

Reported here are the results of combining F-LR with two methods to inactivate any immunogenic WBCs not removed by filtration; i.e., either gamma-irradiation (γ-I) or MIRASOL® pathogen reduction (MPR). (6) These combined methods were evaluated when applied to platelet-rich-plasma (PRP), applicable to apheresis platelets, or to whole blood (WB) prior to preparation of platelet concentrates.

Materials and Methods

Donor/recipient pairs were of different breeds, DLA-DRB incompatible, and a recipient dog received up to 8 weekly treated radiolabeled platelet transfusions from their same single donor, a highly immunogenic stimulus, or until platelet refractoriness. Baseline and weekly recipient serum samples were tested for platelet and lymphocyte antibodies by flow cytometry.

Experimental Animals

Dogs were housed at the University of Washington Vivarium and experiments approved by an Animal Committee. Kennel bred virgin mongrel hounds and beagles were used as donors and recipients, respectively [Marshall Bioresources (North Rose, NY) or Ridglan Farms (Mt. Horeb, WI)].

Preparation of Donor Platelets

Untreated Standard (STD)

In this procedure, 30 to 60 mls of whole blood (WB) were centrifuged for 15 minutes at 234 g, PRP was expressed and centrifuged at 935 g for 15 minutes, supernatant expressed, and the platelets re-suspended.

Treated

PRP was F-LR with PALL® PL1-B or FENWAL® PLS-5A filters or γ-I with 25 Gy (GammaCell 1000 Irradiator; Mississauga, Ontario, Canada). For MPR, 5 mls or 3.5 mls of riboflavin were added to 50 mls of PRP or WB, respectively, before exposure to 100 Joules/mL using a UV irradiator (TERUMO® BCT; Lakewood, CO).

Two methods of assessing MPR WB were used: 1) WB was MPR and PRP prepared from WB was PL1-B F-LR; or 2) WB was F-LR using a platelet-sparing filter (IMUFLEX® WB-SP, TERUMO® BCT; Lakewood C0)(7) followed by MPR of the WB.

Radiolabeling of Donor Platelets

After treatment, platelets were isolated from the PRP or WB as per STD platelets, radiolabeled with $^{51}$Chromium, and injected within 8 hours of collection. (8) Blood samples were drawn 15-30 minutes after transfusion, daily for 3 days, and sample radioactivity determined [Wallac 1480 Wizard 3" Gamma Counter (Turku, Finland)]. Platelet survival was calculated using weighted means and recoveries determined from the survival curve at 20 hours. (9)

Platelet and White Blood Cell (WBC) Counts of the Platelets

Automated platelet and WBC counts were performed [ABX Micros 60 hematology analyzer, (Horiba Medical, CA)]. The lower sensitivity for WBCs was 1×106 per transfusion.

Antibody Detection

Baseline, weekly, and study completion recipient serum samples were frozen at −80° C. and batch tested, along with antibody positive and negative sera, against donor and autologous fresh platelets and lymphocytes. Flow cytometry detected bound IgG using anti-dog IgG-fluorescein isothiocyanate (Jackson Laboratories; West Grove, PA). (10) By gating on characteristic size and complexity, 10,000 lymphocyte and 20,000 platelet events were analyzed for FL-1 intensities for platelet IgG, Phycoerythrin (PE) for B-cells, and F1-4 for CD8 cells (FACScan, Lysis II, Becton-Dickinson; San Jose, CA). Using a 1024 channel scale, recipient sera≥1.3 above autologous sera were considered antibody positive.

DLA-DR-B Typing

An oligotyping assay was developed which utilizes allele discriminating oligonucleotide probes immobilized on nylon membranes. (1,3,11-13) DR-B testing allowed assess to major histocompatibility matching between donor and recipient pairs. Whenever possible, DR-B completely mismatched donors were selected and recipients as matching. Such methods, in some aspects, are associated with high rates of tolerance.

Trial Design

Donor/Recipient Pairs

Crossmatch negative and DLA-DRB mismatched donor/recipient pairs were selected, the latter to decrease tolerance. (14-16)

Platelet Refractoriness

Eight weekly donor platelet transfusions were given or until refractoriness, defined as 2 sequential 20-hour post-transfusion platelet recoveries of ≤5%. Platelets were accepted until their first refractory transfusion. Accepting recipients received up to 8 additional weekly STD transfusions from their same donor or until refractoriness to assess donor specific tolerance.

Statistical Methods

Time to refractoriness was assessed using Kaplan Meier curves and analyzed by log-rank test. Comparisons between treatments were analyzed using Fisher's exact test. Comparisons of 20 hour recoveries at different times within each group were evaluated by fitting linear mixed effects models to recovery values with the recipient dog serving as the model's random effect.

Results

Neither γ-irradiation (γ-I) nor MIRASOL® pathogen reduction (MPR) of donor platelets prevented alloimmune platelet refractoriness; 0% and 14% accepting recipients, respectively. Unfortunately, when γ-I was added to F-LR platelets, acceptance rates actually decreased from 46% to 20%. In contrast, when MPR was added to F-LR platelets, $^{21}/_{22}$ (95%) recipients accepted these platelets. Furthermore, $^{7}/_{21}$ (33%) accepting recipients demonstrated specific tolerance to an additional 8 weekly non-treated donor transfusions. Platelet concentrates prepared from F-LR/MPR whole blood (WB) were also non-immunogenic; i.e., 10/10 (100%) accepting recipients. Among 32 recipients who received F-LR/MPR platelets, 31 accepted (97%) with no lymphocyte antibodies, and only 2 developed platelet antibodies not associated with refractoriness.

Transfused Platelets

Platelets averaged 1.0 to 2.7×109/transfusion. WBCs/transfusion averaged 6.7×106 for standard transfusions (STD) and ≤1×106 for F-LR transfusions.

Radiolabeled Autologous and Donor Platelet Recovery and Survival

All 59 recipients had baseline radiolabeled autologous platelet recoveries and survivals, averaging 49±10% and 5.1±1.2 days, respectively, Forty recipients (68%) had repeat post-study recoveries of 52±8% (106% of baseline) and survivals of 5.2±1.0 days (102% of baseline) or 5.0±0.8 days (97% of their baseline data), indicating no change in the recipients' clinical condition that could have affected donor transfusion responses. Therefore, any refractoriness was considered immune mediated even without detectable antibodies.

There were no adverse effects of γ-I when used alone or when added to F-LR on either autologous platelet recoveries or survivals (Table 10). In contrast, MPR alone reduced both autologous platelet recoveries and survivals to 45% and 37% of their baseline values, respectively. However, when platelets were PL1-B F-LR or PLS-5A F-LR followed by MPR, recoveries improved to 94% and 62% and survivals to 40% and 33% of their baseline values, respectively. Furthermore, when WB was F-LR/MPR, autologous platelet recoveries were 85% and survivals were 91% of baseline values. These data clearly demonstrate the benefits of combining F-LR with MPR.

Data are also provided on the post-transfusion recoveries and survivals of the donor's platelets from the first transfusion until refractoriness (Table 10). Even the first post-transfusion donor platelet recoveries, as a percentage of the recipient's autologous recoveries, were so low for γ-I (34%), MPR (32%), and PALL® PL1-B/γ-I (17%) transfusions, platelet survivals could not be determined. For FENWAL® PLS-5A/γ-I platelets, first donor recoveries and until refractoriness averaged 60% and 67% and survivals 87% and 65% of their recipient's autologous data, respectively.

Interestingly, first donor platelet recoveries were better for F-LR/MPR/γ-I transfusions than for F-LR/MPR transfusions without γ-I (82% versus 49% of autologous recipients' baseline data, respectively, p=0.03), and this difference continued for 8 weeks (87% versus 53%, respectively, p=0.02). Similarly, there were also differences in platelet survivals between the F-LR/MPR/γ-I and the F-LR/MPR donor transfusions; i.e., 46% versus 35% of autologous recipients' baseline data, respectively (p=0.07) for first donor survivals and 47% versus 35% of autologous recipients' baseline data until refractoriness, respectively (p=0.007).

For MPR WB, first donor platelet recoveries, as a percentage of autologous baseline recoveries, were the same for F-LR/MPR WB and MPR WB/F-LR PRP (49% versus 34%, respectively, p=0.32) as were platelet survivals (89% versus 40%, respectively, p=0.16), and the comparability between the groups continued until refractoriness.

TABLE 10

RECOVERIES AND SURVIVALS OF AUTOLOGOUS AND DONOR PLATELETS

| | PLATELET | | | | | | | | | |
|---|---|---|---|---|---|---|---|---|---|---|
| | Recoveries (%) | | | | | Survivals (Days) | | | | |
| Platelet Treatment | Autologous Transfusions (Baseline) | 1st Donor Transfusions (% of Baseline) | Donor Transfusions Until Platelet Refractory (% of Baseline) | Autologous Transfusions [Post-Donor Transfusions (% of Baseline) | Treated Autologous Transfusions (% of Baseline) | Autologous Transfusions (Baseline) | 1st Donor Transfusions (% of Baseline) | Donor Transfusions Until Platelet Refractory (% of Baseline) | Autologous Transfusions [Post-Donor Transfusions (% of Baseline) | Treated Autologous Transfusions (% of Baseline) |
| PLATELET TREATMENT Single Treatment: F-LR: | | | | | | | | | | |
| F-LR PALL ® PL1-B | 51 ± 6 | 27 ± 18 (53) | 27 ± 17 (53) | 51 ± 10 (100) | 56 ± 8 (110) | 5.0 ± 0.5 | 2.9 ± 1.5 (58) | 2.7 ± 1.2 (54) | 4.9 ± 0.3 (98) | 5.1 ± 0.9 (102) |
| F-LR PALL ® PLS-5A | 39 ± 6 | 38 ± 21 (97) | 32 ± 13 (82) | 43 ± 90 (110) | ND | 3.9 ± 0.5 | 5.3 ± 3.7 (143) | 3.4 ± 3.2 (87) | 4.1 ± 0.7 (105) | ND |
| γ-Irradiation | 47 ± 11 | 16 ± 6 (34) | 14 ± 5 (30) | 49 ± 9 (104) | 44 ± 9 (94) | 5.6 ± 1.6 | NR | NR | 5.4 ± 1.6 (96) | 5.2 ± 1.7 (93) |
| MIRASOL ® | 47 ± 5 | 15 ± 13 (32) | 14 ± 10 (30) | 48 ± 11 (102) | 21 ± 7 (45) | 5.4 ± 1.1 | NR | NR | 5.2 ± 0.7 (96) | 2.0 ± 0.6 (37) |
| Combined Treatments: γ-Irradiation: | | | | | | | | | | |
| Plus PALL ® PL1-B filter | 47 ± 6 | 8 ± 4 (17) | 10 ± 5 (21) | 51 ± 5 (109) | 37 ± 18 (79) | 4.8 ± 0.7 | NR | NR | 4.5 ± 0.5 (94) | 3.1 ± 0.9 (65) |
| Plus FENWAL ® PLS-5A Filter MIRASOL ®: | 43 ± 5 | 26 ± 19 (60) | 29 ± 19 (67) | 47 ± 2 (109) | 48 ± 7 (111) | 5.2 ± 0.9 | 4.5 ± 3.0 (87) | 3.4 ± 2.5 (65) | 4.7 ± 0.5 (90) | 4.6 ± 0.8 (88) |

Platelet Acceptance Rates

DLA-DRB Matching

As planned, 52/59 pairs (88%) were DLA-DRB mismatched, and 7 pairs shared one epitope. For the 7 haploidentified pairs, there were no observable effects on transfusion outcomes. Epitope sharing did not increase acceptance of either treated or subsequent transfusions of STD platelets given to assess specific tolerance.

Single Treatments of PRP

Figure 7A:
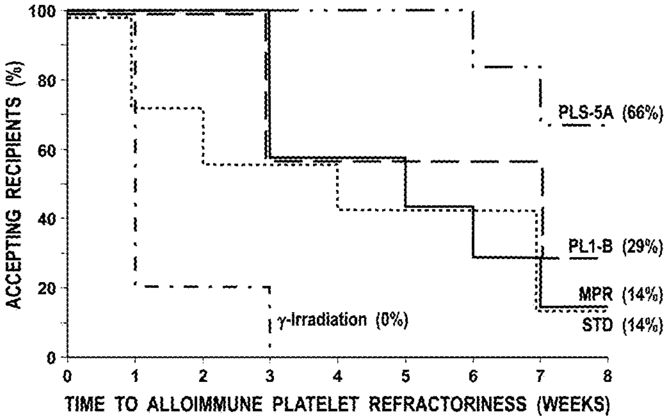
FIGS. 7A-7C provide plots of time to refractoriness versus percentage of accepting recipients. More specifically, FIG. 7A provides a plot showing duration of acceptance of single treatments of donor platelet transfusions. Shown in the figure are the number of weeks that recipient dogs accepted donor platelets that have not been treated (standard ··········), PLS-5A F-LR (▬ ▪ ▪ ▪), PL1B F-LR (▬ ▬) MIRASOL® pathogen reduced (MPR) (━━━━), or γ-irradiated (▬ ▪ ▬ ▪). Time to refractoriness was significantly shorter for STD and MPR platelets compared to PLS-5A F-LR platelets (p≤0.04), and for γ-I platelets compared to all other groups (p<0.04). Time to refractoriness was significantly longer for PLS-5A F-LR platelets compared to STD and MPR platelets (p≤0.04), and for all types of platelets compared to γ-I platelets (p<0.04). Of note, it was 3 weeks before any recipient became refractory to MPR and PL1-B F-LR platelets and 6 weeks to become refractory to PLS-5A F-LR platelets. In contrast, 80% of the recipients of γ-I transfusions became refractory after a single transfusion. Data for STD, PLS-5A, and PL1-B F-LR transfusions have been previously reported and are given here as reference. Also, FIG. 7B provides a plot showing duration of acceptance of combined treatment of donor platelet transfusions. As shown, the number of weeks that recipient dogs accepted donor platelets was significantly shorter for PL1-B F-LR/γ-I (··········) versus either PL1-B F-LR/MPR (━━━━)(or PLS-5A/MPR platelets (▬ ▪ ▪ ▬) (p<0.003), significantly shorter for PLS-5A F-LR/γ-I (▬ ▬) versus PL1-B/MPR (p=0.02) but not versus PLS-5A/MPR platelets (p=0.08), and not between PL1-B F-LR/γ-I versus PLS-5A F-LR/γ-I transfusions (p=0.48). Furthermore, FIG. 7C provides a plot showing duration of acceptance of donor platelets prepared from MPR treated WB. The number of weeks that recipient dogs accepted donor platelets that were prepared from MPR WB followed by PL1B F-LR of PRP (▬ ▬) was significantly shorter than platelets prepared from F-LR WB followed by MPR of the WB (━━━━)(p=0.006). However, even MPR WB/PL1-B PRP platelets were accepted for at least 4 weeks.
Figure 8A:
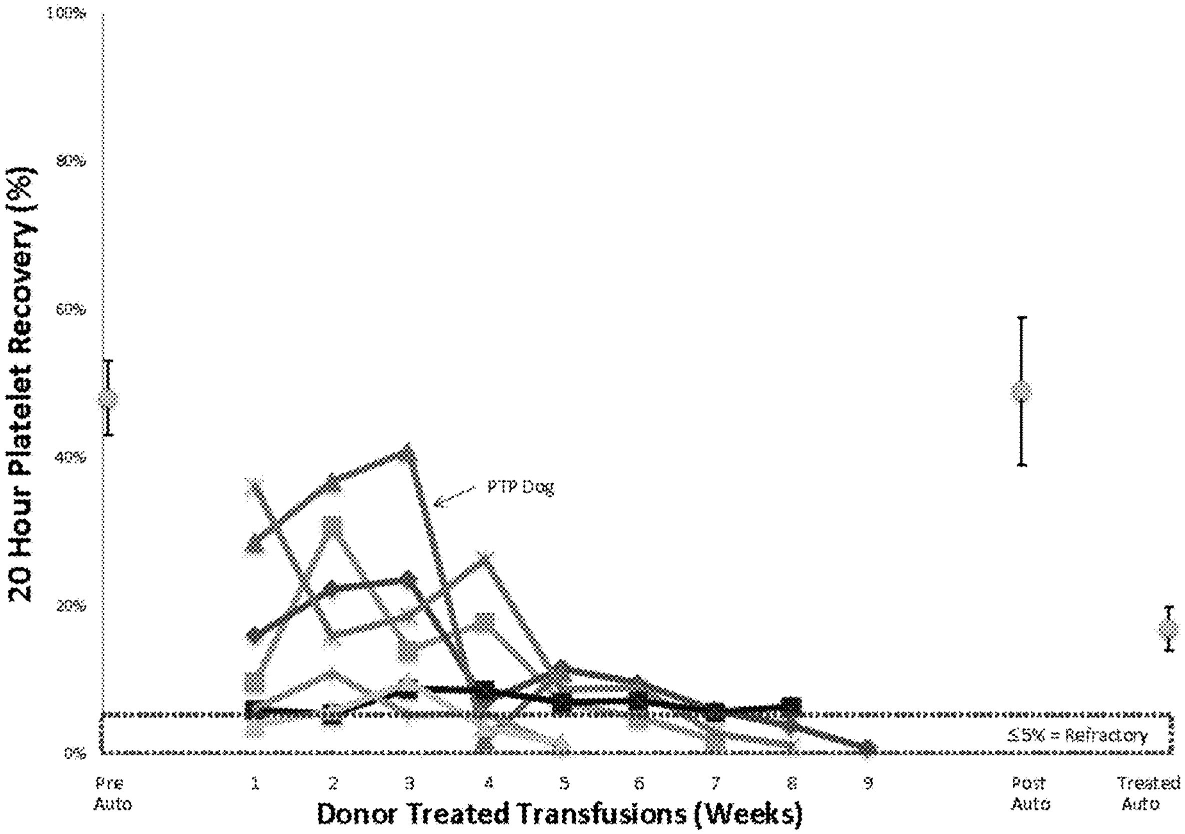
FIGS. 8A-8B provide plots of percent platelet recovery versus time relating to donor treated transfusions, and more specifically, 20 hour donor platelet recoveries of single treatments of PRP.
Figure 8B:
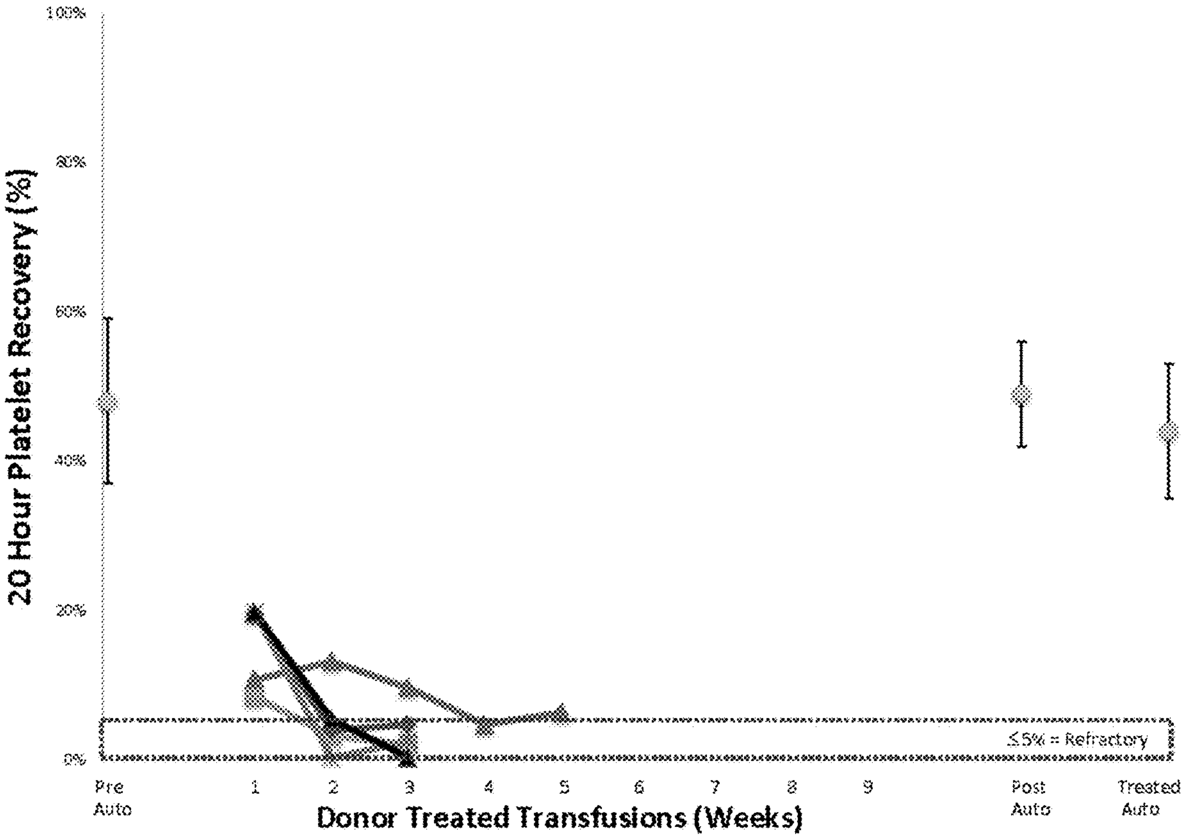

In prior studies, recipient platelet acceptance rates were 1/7 (14%) for STD, (1) 2/7 (29%) PL1-B F-LR, (3) and 4/6 (66%) PLS-5A F-LR. (3) In the present study, recipient acceptance rates for MPR and γ-I platelets were 1/7 (14%) and 0/5, respectively (Table 8, generally showing acceptance of donor platelet transfusions). Small numbers precluded any significant differences. Time to refractoriness was significantly reduced for MPR and STD platelets compared to PLS-5A ($p \leq 0.04$) and for γ-I compared to all other transfusions ($p<0.04$) (FIG. 7A). Recipient responses were very poor for MPR and γ-I transfusions (FIGS. 8A and 8B, respectively).

Figure 7B:
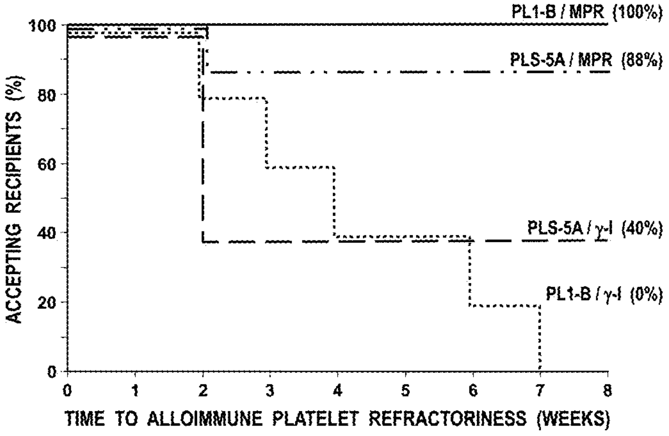

F-LR/MPR had no adverse effect; 7/7 recipients accepted. Overall, 21/22 recipients (95%) accepted F-LR/MPR platelets with no differences among the filters. Time to refractoriness was significantly longer for F-LR/MPR versus F-LR/γ-I platelets ($p=0.001$) (FIG. 7B). Time to refractoriness for PL1-B F-LR/γ-I platelets was significantly less than any F-LR/MPR platelets ($p<0.003$) but not for PLS-5A F-LR/γ-I versus PLS-5A/MPR platelets ($p=0.08$). Furthermore, transfusion responses to F-LR/MPR platelets were much better than MPR platelets alone (FIGS. 9A-9C versus FIG. 8A). Recoveries of F-LR/MPR or F-LR/MPR/γ-I donor platelets were consistently good.

WB

Figure 7C:
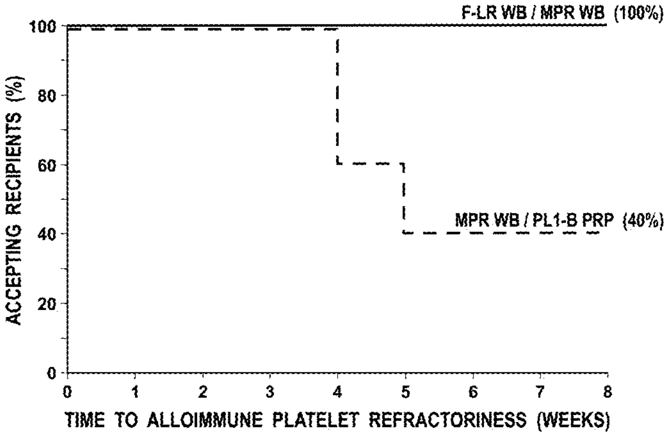
Figure 9A:
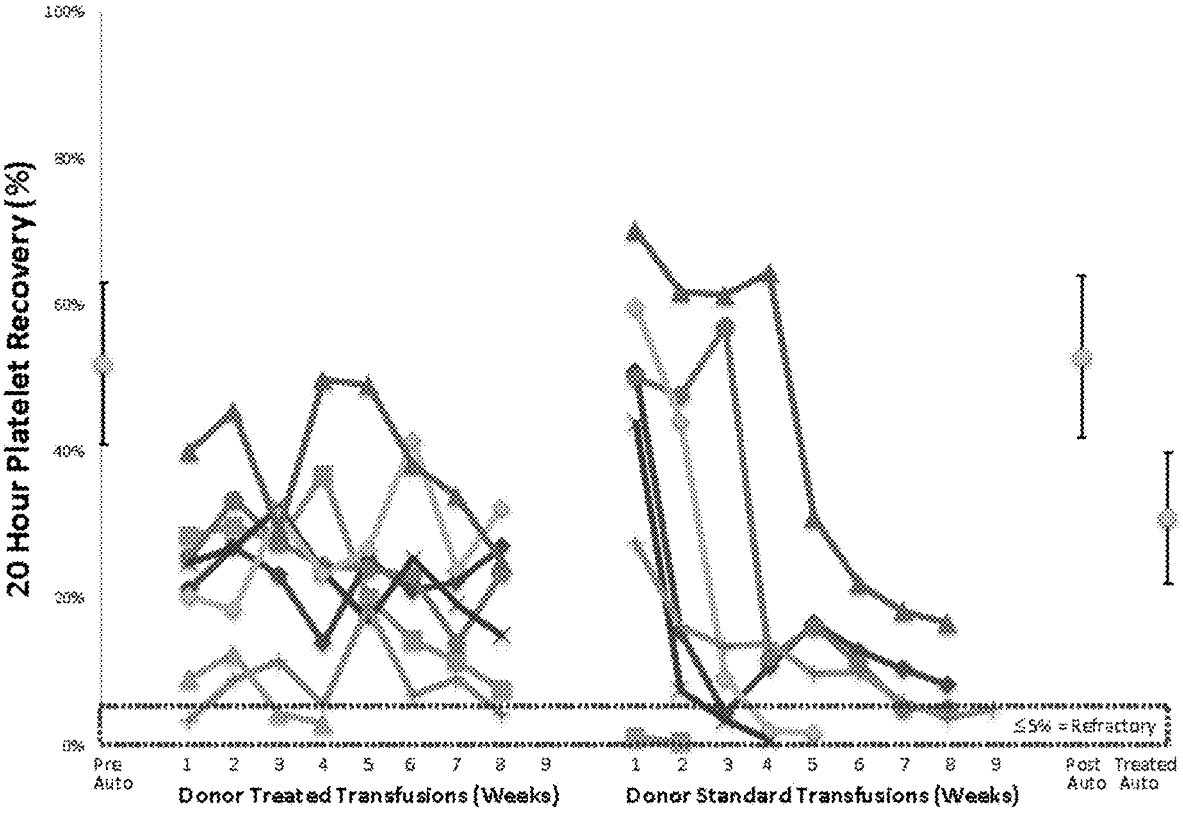
FIGS. 9A-9C provide plots of percent platelet recovery versus time relating to donor treated and standard transfusions and more specifically, illustrate 20 hours donor platelet recoveries for platelets prepared from combined treatments of PRP.
Figure 9B:
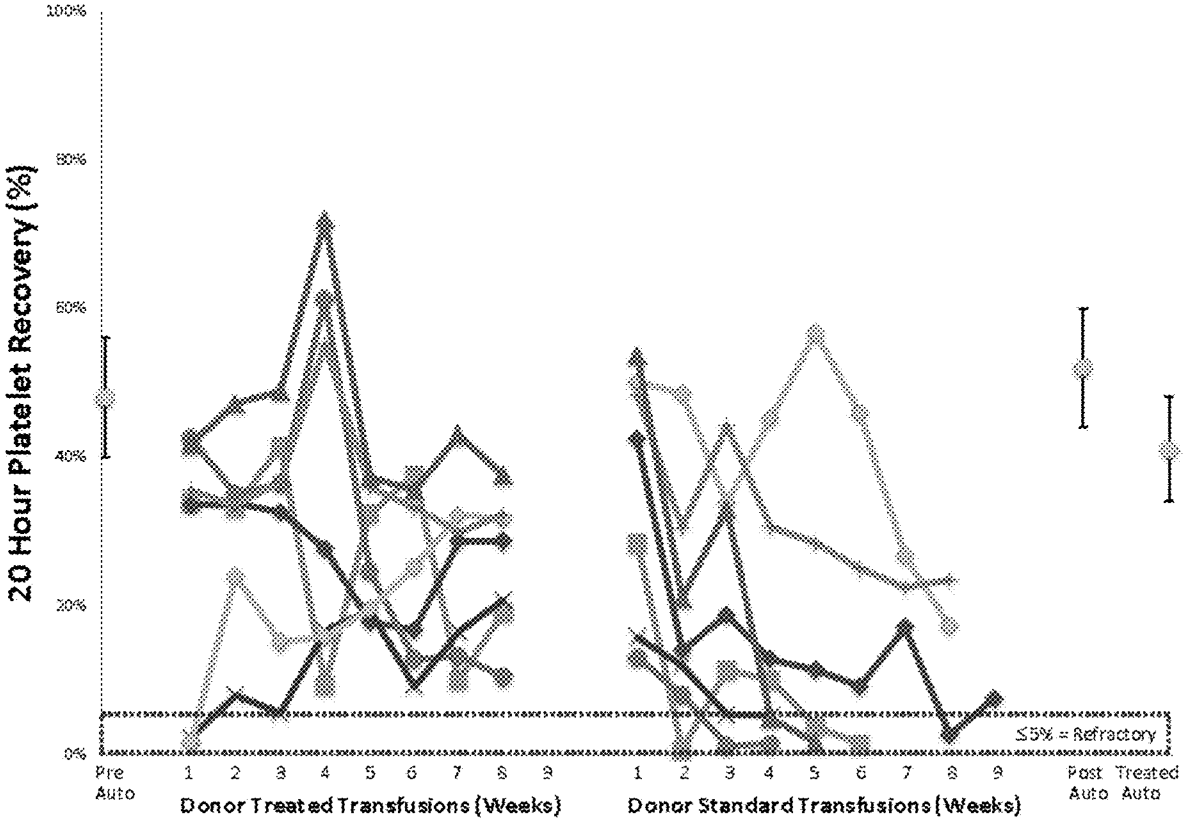
Figure 9C:
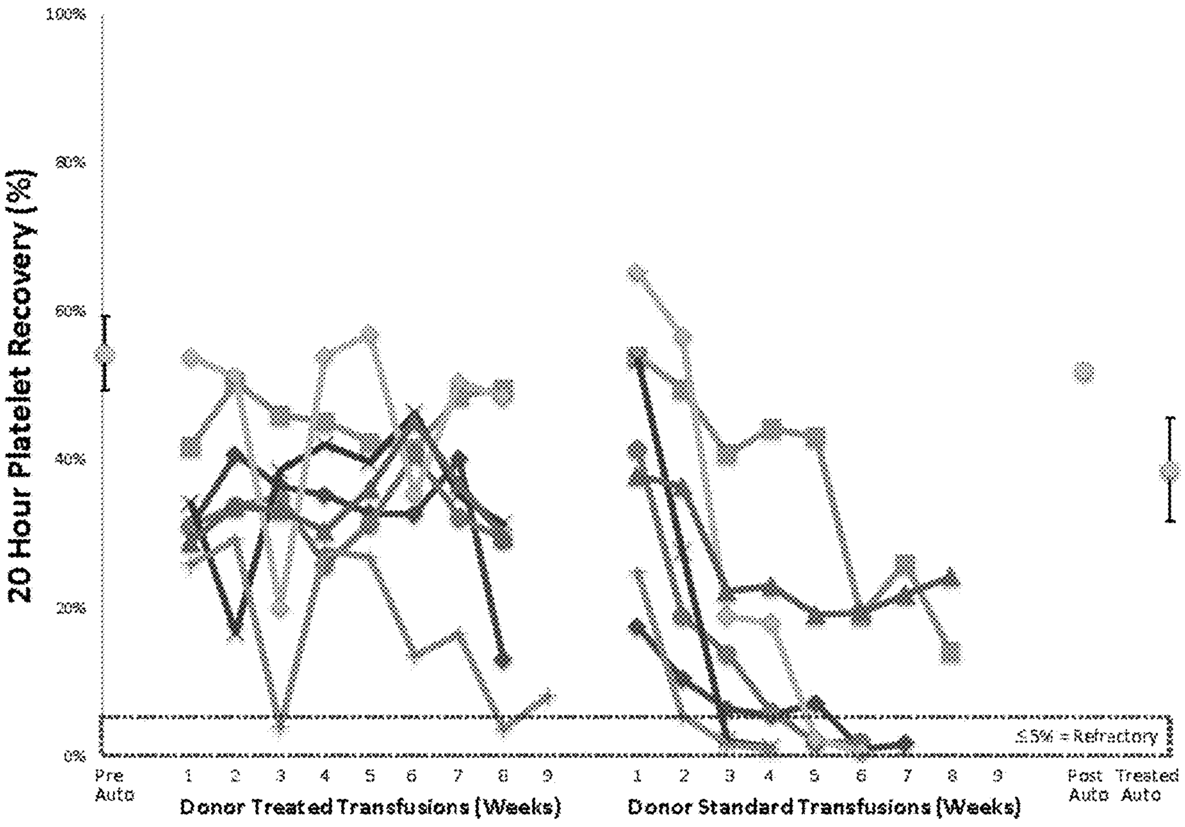
Figure 10A:
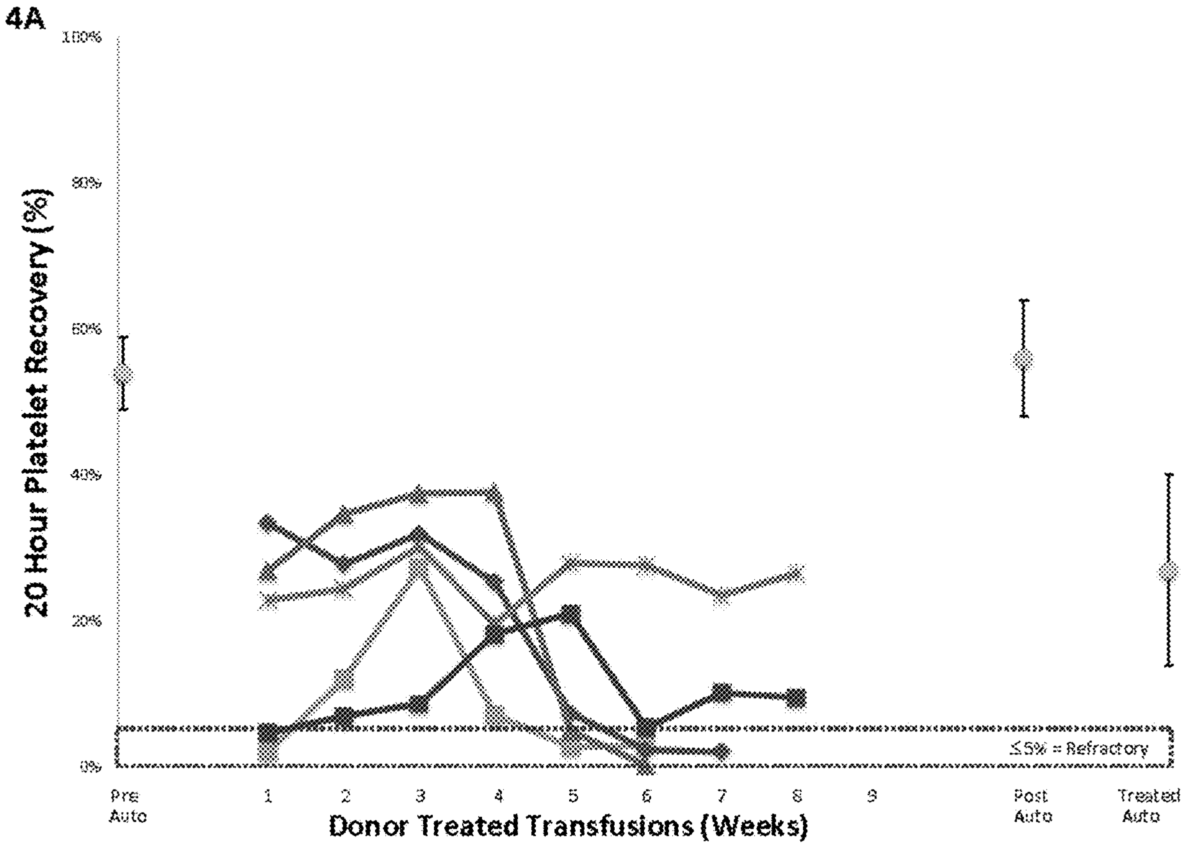
FIGS. 10A and 10B provide plots of percent platelet recovery versus time relating to donor treated transfusions, and more specifically, illustrate 20 hour donor platelet recoveries for platelets prepared from MPR WB.
Figure 10B:
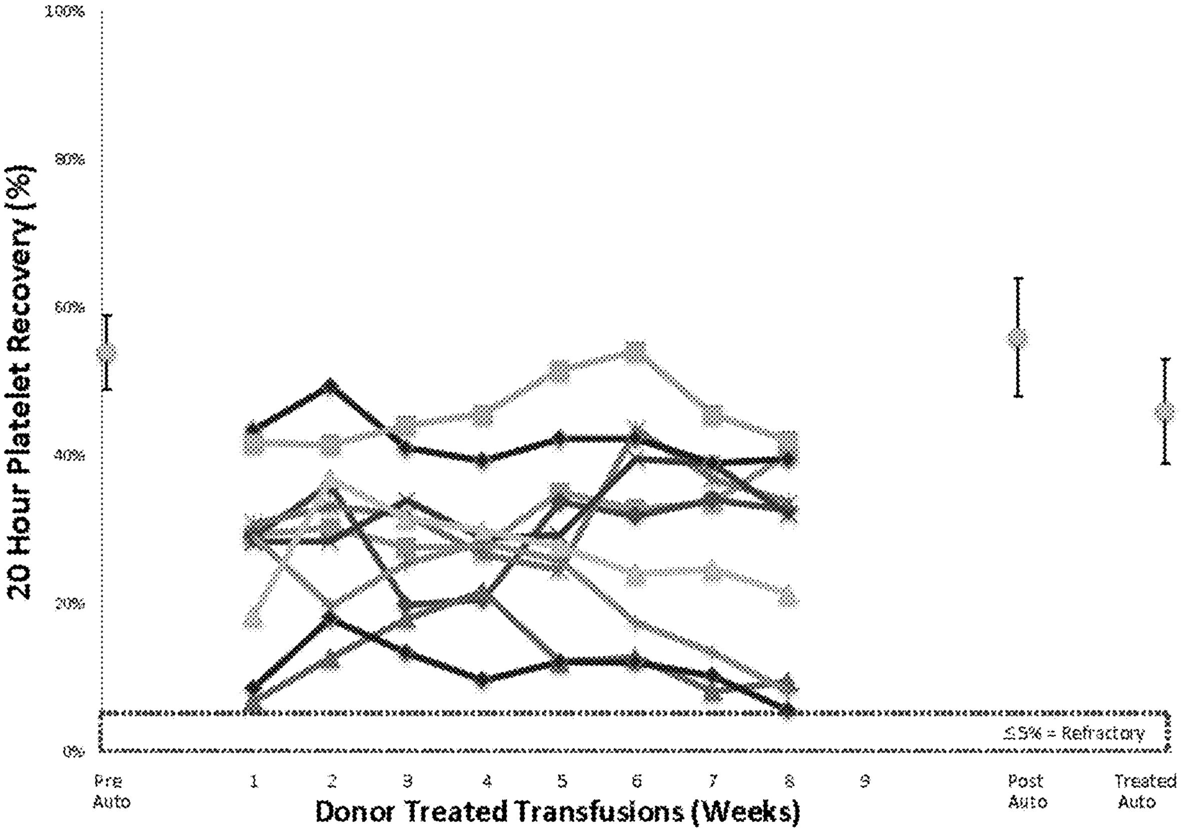

MPR of WB followed by PL1B F-LR of PRP prepared from WB resulted in 2/5 (40%) accepting recipients (Table 8, FIG. 10A). Alternatively, if WB was F-LR followed by MPR of WB, 10/10 (100%) recipients accepted WB-derived platelets, comparable to acceptance of F-LR/MPR PRP platelets (95%). Acceptance rates and time to refractoriness were significantly longer for the second compared to the first WB process ($p<0.01$ and $p=0.02$, respectively) (FIG. 7C). Transfusion responses to F-LR/MPR WB derived platelets (FIG. 10B) were very similar to F-LR/MPR PRP platelets (FIGS. 9A-9C).

TABLE 8

| Treatment | TREATED TRANSFUSIONS # Donors Accepted/ # Recipients (%) | STANDARD TRANSFUSIONS TO EVALUATE TOLERANCE # Donors Accepted/ # Recipients (%) |
|---|---|---|
| PLATELET (PRP) TREATMENT | | |
| Single Treatment: | | |
| Standard (STD)* | 1/7 (14%) | ND |
| Filter Leukoreduced (F-LR): | | |
| F-LR PALL ® PL1-B* | 2/7 (29%) | 0/2 (0%) |
| F-LR PALL ® PLS-5A* | 4/6 (66%) | 2/4 (50%) |
| Total | 6/13 (46%) | 2/6 (33%) |
| MIRASOL ® Pathogen Reduction (MPR) | 1/7 (14%) | 1/1 (100%) |
| γ-Irradiation (γ-I) | 0/5 (0%) | ND |
| Combined Treatments:** | | |
| γ-I: | | |
| Plus FENWAL® PLS-5A F-LR | 2/5 (40%) | 1/2 (50%) |
| Plus PALL ® PL1-B F-LR | 0/5 (0%) | ND |
| Total | 2/10 (20%) | 1/2 (50%) |
| MPR: | | |
| Plus FENWAL ® PLS-5A F-LR | 7/8 (88%) | 2/7 (30%) |
| Plus γ-Irradiation | 4/4 (100%) | 2/4 (50%) |
| Total | 21/22 (95%) | 7/21 (33%) |
| WHOLE BLOOD (WB) TREATMENT | | |
| MPR of WB Followed By PL1-B F-LR Of PRP | 2/5 (40%) | ND |
| Filtration Of WB Followed By MPR Of WB | 10/10 (100%) | ND |

*Results for the standard(1) and F-LR platelet transfusions(3) have been previously reported and are given here as reference.

**All combined treatments of PRP were first F-LR followed by γ-I or MPR. For F-LR/MPR that were also γ-I, γ-I was done last.

ND—Not done.

Combined Treatments

Platelets

Because of poor acceptance of single treatments, F-LR was combined with either γ-I or MPR. (6) Adding γ-I reduced acceptance rates of F-LR transfusions, from 6/13 (46%)(3) to 2/10 (20%) ($p=0.39$) (Table 8). Recoveries of F-LR/γ-I platelets were very poor.

In contrast, 14/15 recipients accepted F-LR/MPR platelets compared to F-LR/γ-I ($p<0.001$). Interestingly, adding γ-I to Tolerance Induction Too few recipients accepted γ-I, MPR, and F-LR/γ-I platelets to assess tolerance. For recipients who accepted F-LR/MPR PRP platelets, 7/21 (33%) subsequently accepted their donor's STD transfusions (Table 8 and FIGS. 9A-9C).

The acceptance rates of STD platelets were the same for both filters when used with or without γ-I.

Antibody Results

Following MPR or γ-I platelet transfusions, $^{11}/_{12}$ (92%) recipients became platelet refractory, and, of the 10 antibody tested, 8 developed antibodies to donor lymphocytes, 7 to platelets, and 2 were antibody negative (Table 9). The one MPR accepting recipient had both donor lymphocyte and platelet antibodies. One MPR recipient developed post-transfusion purpura after the fifth transfusion with very high antibodies to both the donor's platelets (2.2×autologous control sera) and lymphocytes (1.7×autologous control sera) (FIG. 8A).

Of the 31 recipients who accepted their donor's F-LR/MPR platelets prepared from either PRP or WB, 30 were antibody tested and none had antibodies to donor lymphocytes and only 2 had platelet antibodies not associated with platelet refractoriness (Table 9). As such, among the $^{31}/_{32}$ recipients (97%) who accepted F-LR/MPR PRP or WB derived platelets, 30 were antibody tested; $^{0}/_{30}$ and $^{2}/_{30}$ (7%) were antibody positive to donor lymphocytes and platelets, respectively. In contrast, among the 10 recipients given F-LR/γ-I platelets, $^{2}/_{10}$ (20%) accepted; the 2 accepting recipients were antibody negative. Of the 8 refractory recipients, 2 were not tested; of 6 antibody tested, 2 (33%) were antibody negative, 4 (66%) had lymphocyte antibodies, and 2 (33%) had platelet antibodies. Other antibody results are given in the legends to FIGS. 8A-8B, 9A-9C, and 10A-10B.

Of the 12 recipients refractory to combined treated donor transfusions, 10 were antibody tested, and 6 had antibodies to donor lymphocytes, 4 to donor platelets, and 3 were negative. Of the 7 recipients who developed tolerance to their donor's STD platelets, 3 had antibodies to both their donor's lymphocytes and platelets and 4 were antibody negative (Table 9). Of the 14 recipients who rejected STD platelets, 13 were antibody tested and 12 developed antibodies to their donor's lymphocytes, 3 to platelets, and 1 was antibody negative.

Overall, for all study transfused recipients, the antibody results correlated with transfusion refractoriness with a sensitivity of 82%, specificity of 76%, positive predictive value of 85%, and negative predictive value of 73%.

Discussion

Our current studies have conclusively demonstrated that F-LR plus MPR eliminates the immunogenicity of contaminating WBCs and platelets in the dog platelet transfusion model. Furthermore, such results will be transferable to man as demonstrated by prior dog studies. (1-4)

Recipient acceptance of donor platelets was chosen as the primary endpoint because of its clinical relevance and antibodies don't always predict transfusion responses. Dog acceptance rates of F-LR platelets that remove WBCs were 29% to 66%. (3) WBC inactivation by MPR or γ-I were 14% and 0% effective, respectively (Table 8).

Combining γ-I with F-LR actually decreased F-LR effectiveness from 46% to 20% but small sample sizes precluded significance ($p=0.39$). In contrast, F-LR/MPR platelets were accepted by $^{14}/_{15}$ recipients (93%) ($p<0.001$ compared to F-LR/γ-I platelets) (Table 8). Although MPR prevented transfusion associated graft-versus-host disease (TAGVHD) in an animal model, (17) some physicians may not accept MPR and γ-I as clinically equivalent in preventing TAGVHD. Therefore, γ-I was added to F-LR/MPR platelets, and 7/7 dogs accepted. Subsequent donor-specific tolerance to 8 weeks of STD platelet transfusions was induced in $^{7}/_{21}$ (33%) recipients who had accepted F-LR/MPR PRP platelets.

MPR of WB followed by F-LR of PRP was only successful in $^{2}/_{5}$ (40%) recipients (Table 8). In contrast, when WB was F-LR followed by MPR of WB, 10/10 (100%) recipients accepted platelets prepared from WB ($p=0.02$). These data may suggest that the majority of the immunogenic white cells must be removed by F-LR before the MPR treatment can inactivate the residual white cells. For the PRP studies, F-LR was performed on the platelets followed by MPR.

Of 32 recipients who received F-LR/MPR platelets from PRP or WB, 31 (97%) accepted. Thirty accepting recipients were antibody tested, and none developed lymphocyte antibodies. However, there is a concern that even with elimination of immunization caused by WBCs, platelets themselves would be immunogenic as they express HLA, platelet specific, and ABO antigens. (18-20) Surprisingly, only 2 recipients (7%) developed platelet antibodies not associated

TABLE 9

| ANTIBODY RESULTS<br>TREATED TRANSFUSIONS | | | | | | | | | | | |
|---|---|---|---|---|---|---|---|---|---|---|---|
| | | ACCEPTING RECIPIENTS | | | | | REFRACTORY RECIPIENTS | | | | |
| | | | Antibody | ANTIBODY POSITIVE | | Antibody | | Antibody | ANTIBODY POSITIVE | | Antibody |
| Treatment—PRP | Enrolled (#) | # | Tested (#) | Lymphocytes (%) | Platelets (%) | Negative (%) | # | Tested (#) | Lymphocytes (%) | Platelets (%) | Negative (%) |
| MPR | 7 | 1 | 1 | 100% | 100% | 0% | 6 | 5 | 80% | 80% | 20% |
| γ-I | 5 | 0 | | | | | 5 | 5 | 80% | 60% | 20% |
| F-LR/γ-I | 10 | 2 | 2 | | | 100% | 8 | 6 | 50% | 33% | 33% |
| F-LR/MPR | 15 | 14 | 13 | 0% | 8% | 92% | 1 | 1 | 100% | 100% | 0% |
| F-LR/MPR/γ-I | 7 | 7 | 7 | 0% | 14% | 86% | 0 | | | | |
| Treatment—WB | | | | | | | | | | | |
| MPR WB/F-LR PRP | 5 | 2 | 2 | | | 100% | 3 | 3 | 66% | 33% | 33% |
| F-LR/MPR WB | 10 | 10 | 10 | | | 100% | 0 | | | | |
| STANDARD TRANSFUSIONS—PRP | | | | | | | | | | | |
| F-LR/MPR | 14 | 5 | 5 | 60% | 60% | 40% | 9 | 8 | 100% | 25% | 0% |
| F-LR/MPR/γ-I | 7 | 2 | 2 | | | 100% | 5 | 5 | 80% | 20% | 20% |

with platelet refractoriness. These results are consistent with TRAP Trial data where platelet antibodies were uncommon (6% to 11%), didn't vary by transfusion group (treated or control), and weren't associated with platelet refractoriness. (4) This 97% acceptance of F-LR/MPR platelets occurred in spite of 8 weekly exposures to the same donor's antigens, a highly immunogenic stimulus, different breeds between donors (mongrel hounds) and recipients (female beagles), and DLA-DRB mismatching (88% of donor/recipient pairs). Two filters that produced different outcomes were also applied when used alone but not when combined with MPR, suggesting that any type of residual WBCs can be inactivated by MPR (Table 8, FIGS. 7A-7B).

There was no effect of γ-I on autologous platelet recoveries as previously observed in humans (FIG. 8B). (21) However, recoveries of even the first γ-I donor transfusion were markedly reduced (31% of auto baseline) and continued to decrease until refractoriness (FIG. 8B), similar to the effects of γ-I donor platelets in TRAP Trial patients; (4) γ-I platelet increments were significantly decreased and refractoriness was significantly increased. (22) Furthermore, adding γ-I to F-LR dog platelets also reduced acceptance rates (Table 8), suggesting that γ-I may actually facilitate alloimmunization as has been observed in a recent patient cardiosurgery study where γ-I of F-LR blood products abrogated the benefits of F-LR in preventing alloimmunization. (23)

MPR reduced autologous platelet recoveries to 55% of their non-treated values (FIG. 8A), consistent with a 25% reduction in human autologous platelet recoveries. (24) Adding F-LR to MPR improved donor recoveries, as expected, since 95% of recipients accepted these transfusions (FIGS. 9A-9C). Autologous recoveries of platelets prepared from F-LR/MPR treated WB were only 15% less than non-treated recoveries; not surprising as the RBCs would have adsorbed some of the UV dose.

Because F-LR/MPR platelets were accepted by 31/32 (97%) recipients, with no lymphocyte antibodies and only 2 with irrelevant platelet antibodies, it is possible that these platelets will be effective in both immunosuppressed and non-immunosuppressed patients; e.g., aplastic anemia or myelodysplasia. F-LR/MPR can also prevent alloimmunization to red cells. F-LR is routinely incorporated into blood center practice, and adding MPR could be easily accomplished. Unfortunately, MPR is not yet platelet licensed in the U.S. but is in Europe. The demonstration that combining F-LR with MPR are equally effective with platelets prepared from PRP and WB suggests they can be utilized for both apheresis platelets and platelet concentrates from WB.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

What is claimed:

1. A method for reducing risk of platelet alloimmunization upon transfusion, the method comprising:

filtering platelet rich plasma (PRP) from a donor through a leukoreduction filter;

performing pathogen reduction on the PRP by adding a photosensitizer compound to the PRP and irradiating the PRP and photosensitizer compound with UV light and thereby substantially eliminating donor lymphocytes from the PRP;

γ-irradiating the filtered and pathogen-reduced PRP; and transfusing the filtered, pathogen-reduced, and γ-irradiated PRP into a recipient, wherein the transfused PRP has an acceptance rate of 90% or higher, and wherein following the transfusion, the recipient is antibody negative to donor lymphocytes; thereby reducing the risk of the recipient developing platelet alloimmunization upon receiving transfused donor platelets.

2. The method according to claim 1, wherein the transfused PRP has an acceptance rate of 93% or higher.

3. The method according to claim 1, wherein the transfused PRP has an acceptance rate of 95% or higher.

4. The method according to claim 1, wherein the risk of the recipient developing platelet alloimmunization upon receiving transfused donor platelets is reduced by 90% or more.

5. The method according to claim 1, wherein the leukoreduction filter is Terumo Immuflex WB-SP.

6. The method according to claim 1, wherein the filtered and pathogen-reduced PRP is transfused into the recipient without undergoing centrifugation.

7. A method of preventing platelet refractoriness in a recipient receiving platelets from an antigenically mismatched donor, the method comprising:

filtering whole blood from a donor through a leukoreduction filter;

performing pathogen reduction on the whole blood by adding a photosensitizer to the whole blood and irradiating the whole blood and the photosensitizer with UV light and thereby substantially eliminating donor lymphocytes from the whole blood; and γ-irradiating the filtered and pathogen-reduced whole blood; and transfusing the γ-irradiated, filtered, and pathogen-reduced whole blood into the recipient, wherein the transfused whole blood has an acceptance rate of 90% or higher, wherein following the transfusion the recipient is antibody negative to donor lymphocytes, and wherein the transfused whole blood do not cause the recipient to develop platelet refractoriness.

8. The method according to claim 7, further comprising the steps of preparing platelet rich plasma or a platelet concentrate from the γ-irradiated, filtered, and pathogen-reduced whole blood; and transfusing the platelet rich plasma or platelet concentrate into the recipient.

9. The method according to claim 7, wherein the UV light is at a wavelength of between 290-370 nm, and/or wherein the photosensitizer compound is a porphyrin, psoralen, dye, acridine, toluidine, flavine, phenothiazine, coumarin, quinolone, quinone, anthroquinone, or riboflavin.

10. The method according to claim 8, wherein the platelet rich plasma or platelet concentrate does not produce an immune reaction in a recipient receiving the platelet rich plasma or platelet concentrate.

11. The method according to claim 9, wherein the dye comprises neutral red, methylene blue, acridine, or toluidines.

12. The method according to claim 8, wherein the platelet rich plasma or platelet concentrate is associated with 80% or less recipient refractoriness.

13. The method according to claim 7, wherein the recipient acceptance of donor platelets of the γ-irradiated, filtered, and pathogen-reduced whole blood is 95% or more and antibodies to lymphocytes are substantially not produced.

14. The method according to claim 7, wherein the recipient accepts donor platelets of the γ-irradiated, filtered, and pathogen-reduced whole blood and antibodies to lymphocytes are not produced.

15. A γ-irradiated, filtered, and pathogen-reduced whole blood produced by the method according to claim 7, wherein the recipient acceptance of donor platelets of the γ-irradiated, filtered, and pathogen-reduced whole blood is 95% or more and antibodies to lymphocytes are substantially not produced.

* * * * *